United States Patent [19]
Brenner et al.

[11] Patent Number: 5,610,281
[45] Date of Patent: Mar. 11, 1997

[54] ANTIBODIES FOR MODULATING HETEROTYPIC E-CADHERIN INTERACTIONS WITH HUMAN T LYMPHOCYTES

[75] Inventors: Michael B. Brenner, Sherborn; Karyn L. Cepek, Brookline, both of Mass.

[73] Assignee: Brigham & Women's Hospital, Inc., Boston, Mass.

[21] Appl. No.: 237,919

[22] Filed: May 3, 1994

[51] Int. Cl.$^6$ .......................... C07K 16/18; C07K 16/24; C07K 16/28; C07K 16/00
[52] U.S. Cl. .................. 530/388.85; 530/387.1; 530/388.1; 530/388.22; 530/388.23; 530/388.75; 424/156.1; 424/141.1; 424/145.1; 424/154.1
[58] Field of Search ........................... 530/388.1, 388.85, 530/388.22, 388.23, 388.75; 424/141.1, 156.1, 145.1, 154.1

[56] References Cited

FOREIGN PATENT DOCUMENTS

WO94/11401  5/1994  WIPO .

OTHER PUBLICATIONS

K. Herrenknecht, K. et al., "Characterization of recombinant E-cadherin (uvomorulin) expressed in insect cells", Journal of Science, 17:147–154 (1993).
Wheelock, M. et al., "Soluble 80-kd fragment of cell-CAM 120/80 disrupts cell-cells adhesion", Journal of Cellular Biochemistry, 34(3):187–202 (1987).
Katayama, M. et al., "Soluble E-cadherin fragments increased in circulation of cancer patients", British Journal of Cancer, 69(3):580–585 (1994).
Parker, C. et al., A family of β7 integrins on human mucosal lymphocytes, (1992) Proc. Natl. Acad. Sci. USA 89:1924–1928.
Geiger, B. et al., Cadherins, (1992) Annual Review of Cell Biology 8:307–32.
Kemler, R., From cadherins to catenins: cytoplasmic protein interactions and regulation of cell adhesion, (1993) Trends in Gastroenterology 9:317–321.
Takeichi M., Cadherins: A molecular family important in selective cell–cell adhesion, (1990) Annual Review of Biochem. 59:237–252.
Takeichi M., Cadherin Cell Adhesion Receptors as a Morphogenetic Regulator, (1991) Science 251:1451–1455.
Nose A. et al., Localization of Specificity Determining Sites in Cadherin Cell Adhesion Molecules, (1990) Cell 61:147–155.
Cepek K. et al., Integrin $\alpha^E\beta7$ Mediates Adhesion of T Lymphocytes to Epithelial Cells, (1993) J. Immunol. 150, 3459–3470.
Kaiserlian D. et al., Expression, function and regulation of the intercellular adhesion molecule–1 (ICAM–1) on human intestinal epithelial cell lines, (1991) Eur. J. of Immunol. 21(10): 2415–2421.
Shimoyama Y. et al., Cadherin Cell–Adhesion Molecules in Human Epithelial Tissues and Carcinomas, (1989) Cancer Research 49(8): 2128–2133.
Vestweber D. et al., Identification of a putative cell adhesion domain of uvomorulin, (1985) EMBO J. 4:3393–3398.
Springer T., Adhesion receptors of the immune system, (1990) Nature 346(6283):425–434.
Springer T., The sensation and regulation of interactions with the extracellular environment: the cell biology of lymphocyte adhesion receptors, (1990) Annual Review of Cell Biol. 6:359–402.
Harris, W. J. et al., TIBTECH, 11:42–44, 1993 Feb.
Osband, M. E. et al., Immunology Today, 11(6):193–195, 1990.
Waldmann, T. A., Science, 252:1657–1662, Jun. 1991.
Shirayoshi, Y et al., Cell Structure and Function, 11: 245–252, 1986.
Karecla, P. I. et al., Eur. J. Immunol, 25:852–856, 1995.

*Primary Examiner*—Susan A. Loring
*Attorney, Agent, or Firm*—Wolf, Greenfield & Sacks, P.C.

[57] ABSTRACT

The invention relates to methods and compositions for modulating the heterotypic adhesion between E-cadherin expressing cells and T lymphocytes. Monoclonal antibodies which specifically bind to E-cadherin and isolated peptides which mimic the binding function of E-cadherin also are provided. The antibodies and peptides are useful in screening assays to identify pharmaceutical lead compounds which are capable of modulating adhesion between T lymphocytes and E-cadherin expressing cells. Methods and pharmaceutical compositions for modifying the mucosal immune response of a subject also are provided.

7 Claims, No Drawings

ANTIBODIES FOR MODULATING HETEROTYPIC E-CADHERIN INTERACTIONS WITH HUMAN T LYMPHOCYTES

GOVERNMENT SUPPORT

This invention was made in part with government support under grant number AI07306 from the National Institutes of Health.

FIELD OF THE INVENTION

This invention relates to methods and compositions for modulating adhesion between cells that express E-cadherin (e.g., epithelial cells, endothelial cells) and T lymphocytes (e.g., intraepithelial T lymphocytes). In particular, the invention relates to methods and compositions for modulating binding between E-cadherin and heterotypic cognates of E-cadherin, such as $\alpha^E\beta_7$ integrin.

BACKGROUND OF THE INVENTION

The adhesive interactions of cells with other cells and between cells and the extracellular matrix are believed to play 1 critical roles in a wide variety of processes including, for example, modulation of the immune system, regulation of developmental processes and tumor progression and metastasis. These interactions are mediated by adhesion molecules which transduce information from the extracellular to the intracellular matrix.

Three families of adhesion molecules which mediate these interactions have been identified: the integrins, the cadherins and the selectins. In general, adhesion molecules are transmembrane proteins which contain an extracellular domain for interacting with an extracellular matrix or cellular component, a transmembrane domain spanning the cell membrane and a cytoplasmic domain for interacting with one or more cytoskeletal components.

The integrins represent one of the best characterized families of adhesion receptors. Integrins are glycoprotein heterodimers which contain a noncovalently-associated $\alpha$ and $\beta$ subunit. There are fourteen known $\alpha$ subunits and eight known $\beta$ subunits which can pair to form at least twenty different integrin molecules. Several distinct integrin $\alpha$ chains are capable of pairing with one type of $\beta$ chain to form a $\beta$ chain subfamily.

Recently, Parker et al. described a novel integrin heterodimer that is expressed on intra-epithelial T lymphocytes (iIEL), i.e., the population of T lymphocytes located along the basolateral surfaces of the epithelial cells which line the mucosa, adjacent to the epithelial cell basement membrane. (Parker, C. et al. (1992) Proc. Natl. Acad. Sci. USA 89:1924). Originally defined by an antibody which recognizes the human mucosal lymphocyte 1 antigen (HML-1), the novel integrin is present on >90% of intestinal IEL (iIEL) and on approximately 40% of lamina propria T lymphocytes (which lie between the epithelial basement membrane and the muscularis mucosae) (Cerf-Bensussan, N. et al., (1987) Eur. J. lmmunol. 17, 1279–1285). The HML-1 antigen contains a novel $\alpha$ chain (designated $\alpha^E$, for "epithelial associated") associated with a $\beta_7$ chain (Parker, C. et al. (1992) Proc. Natl. Acad. Sci. USA 89:1924). Although the $\alpha^E$ and $\beta_7$ subunits have been cloned, a receptor for the $\alpha^E\beta_7$ integrin has not been identified. (See U.S. patent application Ser. No. 08/199,776, the contents of which are incorporated herein by reference, which discloses the primary structure of the $\alpha^E$ chain and Yuan Q. et al. (1990) Int. Immunol. 2:1097; Erie, D. J. et al., (1991) J. Biol. Chem. 266, 11009–11016, which disclose a HML-1 $\beta_7$ chain clone).

The cadherins play an important role in the establishment and maintenance of intercellular connections between cells of the same type (reviewed in Geiger B. et al. (1992) Annual Review of Cell Biology 8:307; Kemler R. (1993) Trends in Gastroenterology 9:317; Takeichi M. (1990) Annual Review of Biochem. 59:237; Takeichi M. (1991) Science 251: 1451). The cadherins are synthesized as precursors that are cleaved during post-translational processing. The mature cadherins are single chain molecules which include a relatively large extracellular domain (typically divided into five sections or "ectodomains"), a single transmembrane region and a cytoplasmic tail. Sequence analysis of cadherin cDNA clones reveals that the extracellular cadherin amino acid sequence can be divided into three inter-homologous ectodomains ("EC 1-3"), each of which is 110 amino acids in length (Takeichi M. (1990) Annual Review of Biochem. 59:237). Within the ectodomains, characteristic sequences of four to five amino acids (LDRE (amino acids 67–71 of SEQ ID NO:1) and DXNDN) are well conserved among all cadherins. In particular, the sequence DXNDNXP, (amino acids 101–105 of SEQ ID NO:1) present in EC 1-3, is thought to bind divalent calcium and is generally believed to be essential for cadherin function. Two additional, less well conserved domains ("EC 4-5") are located proximal to the membrane. Among the classical cadherins (i.e., P-(placenta), E-(epithelial), and N-(neural) cadherin), the cytoplasmic domain contains the highest degree of homology, followed by the EC-1 domain (Takeichi M. (1990) Annual Review of Biochem. 59:237). The high degree of homology observed for the cytoplasmic domain reportedly is a reflection of the association of cadherins with a group of intracellular proteins, "the catenins", that stabilize cadherin active conformation (Kemler R. (1993) Trends in Gastroenterology 9:317).

It is generally believed that sequences in the EC-1 extracellular domain are necessary to mediate homotypic (i.e., cadherin-to-cadherin) binding. Swapping experiments in which part of the E-cadherin molecule is replaced with a corresponding portion of the P-cadherin molecule have been used to identify the amino acid portions of post-translationally processed cadherin that are required for biological activity. (Nose A. et al. (1990) Cell 61:147). In particular, Nose et al. report that an HAV (amino acids 80–82 of SEQ ID NO:2) tripeptide sequence is essential for homotypic cadherin binding. Further, Takeichi report that the amino acid residues flanking the HAV tripeptide sequence also contribute to homotypic binding specificity. (Takeichi M. (1991) Science 251:1451). A review of the literature indicates that research directed to understanding cadherin-mediated adhesion has focussed on efforts to elucidate the mechanism underlying cadherin-mediated homotypic cell adhesion. Little attention has been directed to understanding what, if any, role is played by cadherin in heterotypic cell-to-cell adhesion.

While it has been known for some time that integrins and other adhesion molecules function in immune system modulation, e.g., by playing a role in the adhesion of peripheral lymphocytes to endothelium and in homing to lymph nodes, relatively little is known regarding the mechanism by which lymphocytes home and transmigrate through the vascular endothelium to specifically target tissue locations. In particular, little is known about the molecules that function in mucosal T lymphocyte homing and adhesion, the subset of the general immune system which includes the lymphocytes which populate the gastrointestinal, genito-urinary and respiratory tracts, and the mammary glands. (see, Cepek, K. et al., (1993) J. Immunol. 150, 3459–3470 and references cited therein). In part, the difficulties encountered in cloning the $\alpha^E$ subunit (described in U.S. patent application Ser. No. 08/199,776) and in obtaining anti-epithelial cell antibodies which block intra-epithelial lymphocyte adhesion have hindered the identification of an epithelial cell receptor for the intra-epithelial lymphocyte $\alpha^E\beta_7$ integrin. An incomplete understanding of the role played by cytokines in modulating $\alpha^E\beta_7$ expression in intra-epithelial cells, also has impeded the identification of a receptor for the $\alpha^E\beta_7$ integrin.

SUMMARY OF THE INVENTION

Compositions and methods for modulating the interaction between a T lymphocyte and an E-cadherin expressing cell are disclosed herein. The interaction is dependent upon the specific binding of E-cadherin to a heterotypic cognate of E-cadherin that is present on the T lymphocyte. Although the homotypic adhesion of one cadherin molecule for another cadherin molecule is well known in the art, the phenomenon of heterotypic cadherin interaction, i.e., the specific binding between cadherin and a non-cadherin molecule, is new.

In view of our observations: (1) that E-cadherin functions as a receptor for $\alpha^E\beta_7$ integrin, an exemplary adhesion molecule that is preferentially expressed in intra-epithelial T lymphocytes ("IEL") and (2) that E-cadherin is expressed on the vascular endothelium, we believe that E-cadherin plays a key role in the interactions between T lymphocytes and E-cadherin expressing cells and in particular, in the interactions of intra-epithelial T cells and epithelial or endothelial cells. Accordingly, the specific examples disclosed herein (primarily directed to fully understanding the interaction between E-cadherin and $\alpha^E\beta_7$) serve as a model for other E-cadherin mediated T lymphocyte adhesion reactions.

Although not intending to be bound by any particular theory, it is believed that E-cadherin mediated binding of T lymphocytes to the vascular endothelium is involved in the migration of lymphocytes into mucosal tissue. It further is believed that the interaction of $\alpha^E\beta_7$ integrin with epithelial cell E-cadherin is involved in the retention of IELs within the epithelium. The dependence of lymphocyte transmigration and adhesion on tissue specific cadherin expression has not previously been reported. Accordingly, the invention provides compositions and methods for inhibiting the transmigration of T lymphocytes through the vascular endothelium into mucosal tissue, and for inhibiting lymphocyte adhesion to E-cadherin expressing epithelial cells. Thus, the invention is useful for modulating a mucosal immune response in vivo.

One aspect of the invention is directed to isolated peptides which inhibit adhesion between T lymphocytes (e.g., IELs) and E-cadherin expressing cells (e.g., epithelial cells, endothelial cells) in vivo and/or in vitro. The peptides specifically bind to "heterotypic cognates of E-cadherin", i.e., non-E-cadherin ligands which specifically bind to E-cadherin. According to one embodiment, the peptides have sequences which are related to, or derived from, the amino acid sequence of the extracellular domain of E-cadherin, i.e., that portion of the E-cadherin protein which is exposed to the extracellular environment when the protein, expressed on mucosal epithelial cells, is in its native conformation. E-cadherin includes an extracellular domain (amino acids 1–552 of Sequence I.D. Nos. 1 and 2), a transmembrane domain (amino acids 553–576) and a cytoplasmic domain (amino acids 577–726). By binding to the heterotypic cognate of E-cadherin on T lymphocytes (e.g., by binding to $\alpha^E\beta_7$ integrin on IEL), the E-cadherin derived peptides inhibit binding of the T lymphocyte to the E-cadherin expressing cell. The peptides can be also specifically reactive with a monoclonal antibody that binds to E-cadherin and that can inhibit T lymphocyte binding.

According to another aspect of the invention, monoclonal antibodies that inhibit adhesion between a T lymphocyte, such as an IEL and an E-cadherin expressing cell, such as an epithelial cell or an endothelial cell, are provided. The monoclonal antibodies specifically bind to a cadherin, more preferably, to E-cadherin. The antibodies are useful for blocking a functional activity of the E-cadherin, such as an in vivo functional activity (e.g., retention of the IELs in the epithelium) or an in vitro functional activity (e.g., adhesion of IELs to an epithelial cell monolayer as determined in an adhesion assay). Accordingly, the antibodies are useful as reagents in assays for screening molecular libraries to identify lead compounds that modulate adhesion between T lymphocytes and E-cadherin expressing cells.

According to yet another aspect of the invention, a pharmaceutical preparation for modulating a mucosal immune response in a subject is provided. The composition includes a pharmaceutically acceptable carrier and an agent that inhibits adhesion between a T lymphocyte and an E-cadherin expressing cell. The agent (e.g., the above-described isolated peptide, isolated E-cadherin or monoclonal antibody) is present in a therapeutically effective amount for treating the mucosal immune response. Preferably, the isolated E-cadherin is soluble E-cadherin.

According to another aspect of the invention, a method for screening a molecular library to identify lead compounds that modulate adhesion between a T lymphocyte and an E-cadherin expressing cell is provided. The method involves performing an adhesion assay (e.g., between an IEL and an epithelial cell) in the presence and absence of at least one member of the molecular library and comparing the adhesion assay results to determine whether the molecular library member modulates adhesion between the T lymphocyte and the E-cadherin expressing cell. The adhesion screening assays of the invention also embrace assays in which an isolated T lymphocyte ligand (alternatively referred to herein as "a heterotypic cognate of E-cadherin") and an isolated receptor E-cadherin (described below) serve as the binding partners in the adhesion assay. Optionally, the isolated receptor E-cadherin and/or its heterotypic cognate may be immobilized onto a solid support, such as a microtiter plate.

According to another aspect of the invention, an antibody assay for screening a molecular library is provided. The assay is useful for identifying pharmaceutical lead compounds that modulate adhesion between a T lymphocyte and an E-cadherin expressing cell. The antibody assay is performed, for example, by contacting a receptor E-cadherin with an antibody (known to specifically bind to the receptor E-cadherin and inhibit the interaction between T lymphocytes and E-cadherin expressing cells) in the presence and absence of at least one member of the molecular library and determining whether the library member modulates binding between the antibody and the receptor E-cadherin. As used herein, a "receptor E-cadherin" refers to an E-cadherin expressing cell, an isolated E-cadherin or an isolated peptide related to, or derived from, the extracellular domain of E-cadherin that is capable of specifically recognizing and binding to a ligand (e.g., $\alpha^E\beta_7$ integrin) expressed on a T lymphocyte.

According to yet another aspect of the invention, a method for inhibiting adhesion between a T lymphocyte and an E-cadherin expressing cell is provided. The method involves contacting the E-cadherin expressing cell with an agent (e.g., the above-described monoclonal antibodies, isolated peptides or isolated E-cadherin) that inhibits adhesion between E-cadherin and its heterotypic cognate.

According to another aspect of the invention, a method for modulating the mucosal immune response of a subject is provided. The method involves administering to the subject a pharmaceutical composition containing the above-described agents for inhibiting adhesion between a T lymphocyte and an E-cadherin expressing cell.

These and other aspects of the invention, as well as various advantages and utilities, will be more apparent with reference to the detailed description of the preferred embodiments.

DETAILED DESCRIPTION OF THE INVENTION

While not intending to be bound by any particular theory, it is believed that E-cadherin modulates the mucosal immune response at two levels: first, by mediating the transmigration of T lymphocytes through the vascular endothelium into mucosal tissue and second, by retaining T lymphocytes within the mucosal epithelium. Accordingly, the experiments described herein were directed to: (1) establishing that E-cadherin is expressed by the vascular endothelium; (2) identifying E-cadherin as an epithelial cell receptor for $\alpha^E\beta_7$ integrin and (3) designing novel agents for inhibiting adhesion between T lymphocytes and E-cadherin expressing cells (and in particular, between IELs and epithelial cells) in vivo and in vitro. The agents of the invention modulate adhesion between T lymphocytes and E-cadherin expressing cells by competing with E-cadherin for binding to a heterotypic cognate of E-cadherin (e.g., $\alpha^E\beta_7$ integrin) that is present on the T lymphocyte, or by specifically binding to E-cadherin in a manner which blocks E-cadherin binding to the heterotypic cognate that is present on a T lymphocyte (e.g., a monoclonal antibody to E-cadherin).

Although the following description is directed to a preferred embodiment of the present invention, namely, compositions and methods for modulating the heterotypic interaction between an IEL and an epithelial cell, it should be understood that this description is illustrative only and is not intended to limit the scope of the present invention. Thus, in its broadest sense, the present invention relates to the discovery that E-cadherin functions as a novel receptor for a heterotypic cognate that is present on T lymphocytes. Accordingly, the compositions and methods disclosed herein are useful for identifying other E-cadherin expressing cells, as well as for identifying other heterotypic E-cadherin cognates that are present in T-lymphocytes.

Agents which modulate adhesion between T lymphocytes (e.g., IELs) and E-cadherin expressing cells (e.g., epithelial cells, endothelial cells, nerve cells, placental cells) are useful for treating autoimmune diseases that are characterized by lymphocyte accumulation at epithelial sites (e.g., ulcerative coliris, Crohn's disease, celiac disease, sarcoidosis, psoriasis, the late phase component of asthma, contact dermatitis, scleroderma, and graft vs. host disease). Such agents also are useful for targeting the delivery of therapeutic agents to the T lymphocytes (e.g., IELs) and/or to the E-cadherin expressing cells (e.g., epithelial cells), thereby permitting the design of more appropriate therapies for treating infectious diseases of epithelial sites (e.g., pulmonary tuberculosis, leprosy, cutaneous leishmaniosis, and parasitic or viral infections diseases of the intestinal tract) by affecting the expression and/or function, for example, of mucosal intra-epithelial lymphocytes or their localization to, or retention in, the epithelium.

According to one aspect of the invention, an isolated peptide that is capable of inhibiting adhesion between a T lymphocyte (e.g., an IEL) and an E-cadherin expressing cell (e.g., an epithelial cell) is provided. The isolated peptide specifically binds to a heterotypic cognate of E-cadherin (e.g., $\alpha^E\beta_7$ integrin), thereby preventing interaction between the cognate of the T lymphocyte and its receptor (E-cadherin) present on the E-cadherin expressing cell. The isolated peptides of the invention are related to, or derived from, the extracellular domain of E-cadherin, i.e., amino acids 1–552 (inclusive) of Sequence I.D. Nos. 1 (cDNA and encoded protein) and 2 (encoded protein).

As used herein in reference to a peptide, the term "isolated" refers to a cloned expression product of an oligonucleotide; a peptide which is isolated following cleavage from a larger polypeptide; or a peptide that is synthesized, e.g., using solution and/or solid phase peptide synthesis methods as disclosed in, for example, U.S. Pat. No. 5,120,830, the entire contents of which are incorporated herein by reference. Accordingly, the phrase "isolated peptides" embraces peptide fragments of the extracellular E-cadherin domain, as well as functionally equivalent peptide analogs (defined below) of the foregoing peptide fragments. A particularly preferred isolated peptide is obtained by isolating the extracellular cleavage product of E-cadherin that results following exposure of epithelial cells to trypsin in the presence of divalent calcium. Trypsin cleavage yields an approximately 80 kD fragment of E-cadherin containing a portion of the extracellular domain. Thus, this particularly preferred peptide has an amino acid sequence corresponding from amino acid 1 to the amino acid positioned at the naturally occurring proteolytic cleavage site of E-cadherin.

As used herein, the term "peptide analog" refers to a peptide which shares a common structural feature with the molecule to which it is deemed to be an analog. A "functionally equivalent" peptide analog is a peptide analog which further shares a common functional activity with the molecule to which it is deemed an analog.

As used herein, the term "functionally equivalent peptide analog" refers to a peptide analog that is capable of inhibiting the binding of a T lymphocyte (e.g., an IEL) to an E-cadherin expressing cell (e.g., an epithelial cell) in vitro by competing with E-cadherin for binding to a heterotypic cognate of E-cadherin, (e.g., $\alpha^E\beta_7$ integrin). Functionally equivalent peptide analogs of E-cadherin are identified, for example, in in vitro adhesion assays (see, e.g., the adhesion assay provided in the Examples) that measure the ability of the peptide analog to inhibit E-cadherin-mediated adhesion between a T lymphocyte and a E-cadherin/expressing cell (e.g., an epithelial monolayer in culture). Such assays are predictive of the ability of a molecule to inhibit this adhesion in vivo. Accordingly, a "functionally equivalent peptide analog" of E-cadherin includes the extracellular domain of E-cadherin, fragments of the extracellular domain and peptide analogs of the extracellular domain (e.g., peptides which contain conservative amino acid substitutions), provided that the peptide fragments and analogs are capable of inhibiting adhesion between a T lymphocyte and an E-cadherin expressing cell in vivo and/or in vitro.

As used herein, "a heterotypic cognate of E-cadherin" refers to a peptide or protein that is present in, or derived from a T lymphocyte, and which specifically recognizes and binds to E-cadherin. The $\alpha^E\beta_7$ integrin is an exemplary heterotypic cognate of E-cadherin. Heterotypic cognates of E-cadherin are useful as reagents in in vitro adhesion assays for screening molecular libraries. Such adhesion assays assess the ability of a molecule (e.g., a molecular library member) to modulate the interaction of two binding partners. Typically, the binding partners are cells which specifically bind to one another via a ligand-receptor mediated mechanism. The cell can be a cell which naturally expresses a binding partner, or can be a cell which is transfected or otherwise genetically altered to express the binding partner.

Alternatively, the binding partners in the adhesion assays can be the particular ligands and receptors which mediate intercellular adhesion. For example, the binding of an IEL to an epithelial cell is mediated via the specific interaction of $\alpha^E\beta_7$ integrin (on the IEL) and E-cadherin (on the epithelial cell). Accordingly, adhesion assays can be performed in which the binding partners are: (1) interacting cells (e.g., an IEL and an epithelial cell); (2) a cell expressing a ligand (e.g., an IEL expressing $\alpha^E\beta_7$ integrin) and an isolated receptor (e.g., E-cadherin) for the ligand; (3) an isolated ligand and a cell expressing the receptor for the ligand; and (4) an isolated ligand and its isolated receptor (e.g., E-cadherin). Thus, a high throughput screening assay for selecting pharmaceutical lead compounds can be performed in which, for example, (1) E-cadherin is immobilized onto the surface of a microtiter well, (2) aliquots of a molecular library containing library members are added to the wells, (3) (labeled) cells expressing a ligand for E-cadherin (e.g., IELs) are added to the wells and (4) the well components are allowed to incubate for a period of time that is sufficient for the IELs to bind to the immobilized E-cadherin. Preferably, the IELs (or other T lymphocytes) are labeled (e.g., preincubated with $^{51}$Cr or a fluorescent dye) prior to their addition to the microtiter well. Following the incubation period, the wells are washed to remove non-adherent cells and the signal (attributable to the label on the remaining T lymphocytes) is determined. A positive control (e.g., no library member present) on the same microtiter plate is used to establish maximal adhesion value. A negative control (e.g., soluble E-cadherin added to the microtiter well) on the same microtiter plate is used to establish maximal levels of inhibition of adhesion.

As used herein with respect to adhesion assays, "T lymphocyte ligand" refers to the isolated heterotypic E-cadherin cognate, a functionally equivalent peptide fragment or analog of the isolated heterotypic E-cadherin cognate, or a cell extracellularly expressing the isolated heterotypic cognate or its functionally equivalent peptide fragment or analog. The $\alpha^E\beta_7$ integrin is an exemplary heterotypic E-cadherin cognate. Similarly, the phrase "receptor E-cadherin" in reference to the adhesion assays of the invention, refers to the isolated E-cadherin, a functionally equivalent peptide fragment or analog of E-cadherin, or a cell extracellularly expressing E-cadherin or its functionally equivalent peptide fragment or analog. The T lymphocyte ligand and/or the receptor E-cadherin can be immobilized on supports, such as microtiter plates or beads, using procedures known to the artisan of ordinary skill in the art.

The screening methods of the invention provide useful information for the rational drug design of novel agents which are, for example, capable of modulating an immune system response. Exemplary procedures for rational drug design are provided in Saragovi, H. et al., (1992) Biotechnology 10:773; Haber E., (1983) Biochem. Pharmacol. 32(13):1967; and Connolly Y., (1991) Methods of Enzymology 203, Ch. 29 "Computer-Assisted Rational Drug Design" pp 587–616, the contents of which are incorporated herein by reference.

Thus, knowledge of the structures (primary, secondary or teriary) of naturally occurring ligands and receptors can be used to rationally choose or design molecules which will bind with either the ligand or receptor. In particular, knowledge of the binding regions of ligands and receptors can be used to rationally choose or design compounds which are more potent than the naturally occurring ligands in eliciting their normal response or which are competitive inhibitors of the ligand-receptor interaction.

Once rationally chosen or designed and selected, the library members may be altered, e.g., in primary sequence, to produce new and different peptides. These fragments may be produced by site-directed mutagenesis or may be synthesized in vitro. These new fragments may then be tested for their ability to bind to the receptor or ligand and, by varying their primary sequences and observing the effects, peptides with increased binding or inhibitory ability can be produced.

Alternatively, the nucleic acid and amino acid sequence of the present invention, i.e., those corresponding to the extracellular domain of E-cadherin, may be used in computer-based modeling systems to predict the secondary and tertiary structure of the extracellular domain. Such computer-based systems are well known to those of ordinary skill in the art of rational drug design. Based upon the tertiary structure of a receptor protein, it is often possible to identify a binding region which is involved in its biological activity. From this information, peptides or other compounds which include or mimic this structure and/or which are capable of binding to it can be rationally designed. In this way, new compounds may be designed which mimic the activity of the receptor or ligand or which will act as competitive inhibitors of the receptor or ligand.

As used herein, "conservative amino acid substitution" refers to an amino acid substitution which does not alter the relative charge or size characteristics of the peptide in which the amino acid substitution is made. Conservative substitutions of amino acids include substitutions made amongst the individual amino acids within the following groups: (a) M, I, L and V (b) F, Y, and W (c) K, R, and H (d) A and G (e) S and T (f) Q and N and (g) E and D.

Peptide analogs include "unique fragments" which are related to, or derived from, the extracellular domain of E-cadherin, polymers of the extracellular domain, and polymers of unique fragments of the extracellular domain. A "unique fragment" of a protein or nucleic acid sequence is a fragment which is not currently known to occur elsewhere in nature (except in allelic or allelomorphic variants). Unique fragments act as a "signature" of the gene or protein from which they are derived. A unique fragment will generally exceed 15 nucleotides or 5 amino acids in length. One of ordinary skill in the art can readily identify unique fragments by searching available computer databases of nucleic acid and protein sequences such as Genbank, (Los Alamos National Laboratories, USA), EMBL, or SWISS-PROT. A unique fragment is particularly useful, for example, in generating monoclonal antibodies or in screening genomic DNA or cDNA libraries.

The peptides of the invention can be specifically reactive with an antibody (preferably a monoclonal antibody) that binds to E-cadherin and thereby inhibits adhesion between E-cadherin and a heterotypic cognate of E-cadherin. In a particularly preferred embodiment, the heterotypic cognate of E-cadherin is $\alpha^E\beta_7$ integrin, or a peptide related to, or derived from, the $\alpha^E\beta_7$ integrin. Preferably, the peptide fragments and/or analogs contain between about three and about one hundred amino acids. More preferably, the peptide analogs contain between about ten and about twenty-five amino acids.

It will be appreciated by those skilled in the art that various modifications of the foregoing peptide analogs can be made without departing from the essential nature of the invention. Accordingly, it is intended that peptides which include conservative substitutions and coupled proteins in which a peptide of the invention is coupled to a solid support (such as a polymeric bead), a carrier molecule (such as keyhole limpet hemocyanin), a toxin (such as ricin) or a reporter group (such as radiolabel or other tag), also are embraced within the teachings of the invention.

According to another aspect of the invention, an antibody that inhibits adhesion between a T lymphocyte (e.g., an IEL) and an E-cadherin expressing cell (e.g., an epithelial cell) is provided. Preferably, the antibody is a monoclonal antibody (e.g., a mouse, chimeric or humanized monoclonal antibody) which specifically recognizes and binds to E-cadherin. Humanized monoclonal antibodies can be prepared by those of ordinary skill in the art using no more that routine experimentation. (See, for example, PCT Application No. US93/02479, Publication No. 93/19197, published Sep. 30, 1993 and N. Lowberg, et al., Nature 368:856–859 (1994), the contents of which publications are incorporated herein by reference.

The antibodies of the invention specifically bind to a cadherin; more preferably, the antibodies binds to E-cadherin. In a particularly preferred embodiment, the antibody is E.4.6 or E6.1 as described in the Examples. The murine hybridoma cell line, E4.6 was deposited under the Budapest Treaty on Nov. 17, 1995 at the American Type Culture Collection, 12301 Parklawn Drive, Rockville, Md. 20852 U.S.A. and accorded ATCC designation HB 11996.

An exemplary protocol for developing anti-epithelial cell hybridomas which specifically bind to E-cadherin is illustrated in the Examples. It has been discovered, surprisingly, that monoclonal antibodies having the above-described adhesion blocking characteristics can be prepared using the particular strain of mice disclosed in the Examples. Efforts to prepare such hybridomas using a more conventional strain of mice (Balb/C) were unsuccessful.

As noted in the Examples, the antibodies were raised against 16E6.A5 epithelial cells harvested with EDTA in the absence of trypsin to preserve proteins containing trypsin cleavage sites (e.g., E-cadherin). Applicants have discovered that expression of E-cadherin by different types of epithelial cells was highly variable and that the successful preparation of monoclonal antibodies was, at least in part, dependent upon selecting the appropriate (i.e., expressing high levels of E-cadherin as determined using the adhesion assay described in the Examples) epithelial cells for immunization. Accordingly, it is believed that the prescreening of epithelial cells for high E-cadherin expression contributed to the successful preparation of the monoclonal antibodies described herein. Mice were immunized with the harvested cells and hybridomas producing anti-epithelial cell monoclonal antibodies were generated through the fusion of spleen cells with myeloma cells at a ratio of four to one. Hybridomas were screened for their ability to block IEL adhesion to epithelial cells.

The monoclonal antibodies of the invention are useful in screening assays identifying pharmaceutical lead compounds in molecular libraries. A "molecular library" refers to a collection of structurally-diverse molecules. Molecular libraries can be chemically-synthesized or recombinantly-produced. As used herein, a "molecular library member" refers to a molecule that is contained within the molecular library. Accordingly, screening refers to the process by which library molecules are tested for the ability to modulate (i.e., inhibit or enhance) adhesion between T lymphocyte (e.g., an IEL) and an E-cadherin expressing cell (e.g., an epithelial cell). As used herein, a "pharmaceutical lead compound" refers to a molecule which is capable of modulating adhesion between the T lymphocyte and the E-cadherin expressing cell. Thus, screening assays are useful for assessing the ability of a library molecule to inhibit the binding of a T lymphocyte (or a T lymphocyte ligand) to an E-cadherin expressing cell (or a receptor E-cadherin).

Libraries of molecularly diverse molecules can be prepared using chemical and/or recombinant technology. Such libraries for screening include recombinantly-produced libraries of fusion proteins. An exemplary recombinantly-produced library is prepared by ligating fragments of E-cadherin cDNA into, for example, the pGEX-2T vector (Pharmacia, Piscataway, N.J.). This vector contains the carboxy terminus of glutathione S-transferase (GST) from *Schistosoma japonicum*. Use of the GST-containing vector facilitates purification of GST-E-cadherin fusion proteins from bacterial lysates by affinity chromatography on glutathione sepharose. After elution from the affinity column, E-cadherin fusion proteins are tested for activity by, for example, contacting at least one fusion protein with an $\alpha^E\beta_7$ integrin-expressing cell prior to (or concurrently with) contacting the integrin-expressing cell with an E-cadherin expressing cell. Fusion proteins which inhibit binding between the integrinexpressing and E-cadherin expressing cells are selected as pharmaceutical lead compounds and/or to facilitate further characterization of the portion of E-cadherin to which the novel integrin binds. See, for example, Koivunen E. et al. (1993) J. Biol. Chem. 268(27):20205 which describes the selection of peptides which bind to the $\alpha^5\beta_1$ integrin from a phage display library.

Antibody-based screening assays are performed by, for example, contacting an antibody (that specifically binds to E-cadherin and inhibits adhesion between a T lymphocyte and an E-cadherin expressing cell) with a receptor E-cadherin in the presence and absence of at least one member of the molecular library and determining whether the library member modulates binding between the antibody and the receptor E-cadherin. In a particularly preferred embodiment, the receptor E-cadherin is an E-cadherin-expressing cell, an isolated E-cadherin or an isolated peptide related to, or derived from, the extracellular domain of E-cadherin.

In a particularly preferred embodiment in which the receptor E-cadherin is E-cadherin, the antibody screening method involves: (1) performing a first antibody assay in the absence of the library molecule to obtain a first antibody assay result; (2) performing a second antibody assay in the presence of the library molecule to obtain a second antibody assay result; and (3) comparing the first and the second antibody assay results to determine whether the molecular library member modulates binding between the antibody and the receptor E-cadherin. According to this embodiment, a second antibody assay result which shows reduced binding between the antibody and receptor E-cadherin indicates that the library member has inhibited binding of antibody to the receptor E-cadherin. Antibody binding assays also can be used to assess the relative affinity of a molecular library member for a heterotypic cognate of E-cadherin, such as $\alpha^E\beta_7$ integrin, using no more than routine experimentation.

The functionally equivalent E-cadherin peptide analogs of the invention also are useful in vivo for blocking transmigration, homing and retention of T lymphocytes, and in particular, are useful in blocking IEL transmigration into and retention in the epithelium. Accordingly, the E-cadherin peptide analogs can be used, for example, for targeting a toxin (e.g., ricin) or a detectable agent (e.g., a radiolabel, a fluorescent label, an enzyme label)to T lymphocytes which express heterotypic cognates of E-cadherin. Methods for coupling such toxins and/or agents to proteins and/or antibodies for in vivo and in vitro applications are disclosed in, for example, Killen and Lindstrom (1984), "Specific killing of lymphocytes that cause experimental Autoimmune Myestenia Gravis by toxin-acetylcholine receptor conjugates", J. lmmun. 133:1335; Jansen, F. K., et al. (1982), "Immunotoxins: Hybrid molecules combining high specificity and potent cytotoxicity", lmmunolog. Rev. 62:185–216, the entire contents of which references are incorporated herein by reference. See also U.S. Pat. Nos. 3,652,761; 4,478,946 and 4,554,088, the entire contents of which patents are incorporated herein by reference.

According to yet another aspect of the invention, a functional assay is provided for screening a molecular library to identify a pharmaceutical lead compound. A particularly preferred functional screening method involves performing an adhesion assay between a T lymphocyte and an E-cadherin expressing cell in the presence and absence of at least one member of the molecular library to determine whether the library member modulates adhesion between the lymphocyte and the E-cadherin expressing cell in vitro. This embodiment involves: (1) performing a first adhesion assay between a T lymphocyte and an E-cadherin expressing cell to obtain a first adhesion assay result; (2) performing a second adhesion assay between the T lymphocyte and the E-cadherin expressing cell in the presence of the library member to obtain a second adhesion assay result; and (3) comparing the first and the second adhesion assay results to determine whether the library member modulates adhesion between the T lymphocyte and the E-cadherin expressing cell. Thus, for example, an adhesion assay result which shows reduced binding between the T lymphocyte and the E-cadherin expressing cell when the assay is conducted in the presence of the library member (compared to the assay result obtained when the assay is performed in the absence of the library member) indicates that the library member inhibits binding of T lymphocytes to E-cadherin expressing cells. An exemplary adhesion assay is provided in the Examples. Other such adhesion assays are well known in the art and can be developed and performed using no more than routine experimentation. Thus, for example, the adhesion assay can be performed by substituting the above-described alternative binding partners, e.g., an isolated ligand and its isolated receptor, for the above-mentioned T lymphocyte and E-cadherin expressing cell.

According to yet another aspect of the invention, methods and compositions for inhibiting adhesion between a T lymphocyte (e.g., an IEL) and an E-cadherin expressing cell (e.g., an epithelial cell) are provided. According to one embodiment, the E-cadherin expressing cells are contacted with an agent that inhibits adhesion between E-cadherin and a heterotypic cognate of E-cadherin (e.g., $\alpha^E\beta_7$ integrin). The agents may be antibodies (preferably monoclonal antibodies) that bind to the extracellular domain of E-cadherin. Alternatively, the agents may be isolated E-cadherin molecules or isolated peptides that specifically bind to the heterotypic cognate of E-cadherin. In one embodiment, the isolated peptides can specifically bind to $\alpha^E\beta_7$ integrin.

According to another aspect of the invention, methods and compositions br modulating a mucosal immune response in a subject are provided. The methods involve administering a pharmaceutical composition containing an agent that inhibits T lymphocyte (e.g., IEL) adhesion to E-cadherin expressing cells (e.g., epithelial cells, endothelial cells). The agent may be an isolated E-cadherin molecule, the above-described isolated peptide and/or the above-described monoclonal antibody. The pharmaceutical composition contains a therapeutically effective amount of agent for treating (i.e., reducing or preventing the mucosal immune response).

In general, the therapeutically effective amount is between about 1 µg and about 100 mg/kg. The preferred amount can be determined by one of ordinary skill in the an in accordance with standard practice for determining optimum dosage levels of the agent. The peptides, E-cadherin, and/or monoclonal antibodies are formulated into a pharmaceutical composition by combination with an appropriate pharmaceutically acceptable carrier. For example, the peptides may be used in the form of their pharmaceutically acceptable salts, or may be used alone or in appropriate association, as well as in combination with other pharmaceutically active compounds. The peptides may be formulated into preparations in solid, semisolid, liquid or gaseous form such as tablets, capsules, powders, granules, ointments, solutions, suppositories, inhalants and injections, in usual ways for oral, parenteral, or surgical administration. Exemplary pharmaceutically acceptable carriers are described in U.S. Pat. No. 5,211,657, the entire contents of which patent are incorporated herein by reference. The invention also includes locally administering the composition as an implant.

The invention also provides isolated oligonucleotides that encode the extracellular domain of E-cadherin (Sequence I.D. No. 1) and functionally equivalent peptide fragments and analogs thereof.

As used herein, the term "isolated" in reference to an oligonucleotide, means an RNA or DNA polymer, portion of genomic nucleic acid, cDNA or synthetic nucleic acid which, by virtue of its origin or manipulation: (a) is not associated with all of a nucleic acid with which it is associated in nature (e.g., is present in a host cell as a portion of an expression vector); or (b) is linked to a nucleic acid or other chemical moiety other than that to which it is linked in nature; or (c) does not occur in nature. By "isolated" it is further meant a nucleic acid sequence: (i) amplified in vitro by, for example, the polymerase chain reaction (PCR); (ii) synthesized by, for example, chemical synthesis; (iii) recombinantly produced by cloning; or (iv) purified from a more complex molecule or from a mixture of molecules, such as by cleavage and size fractionation. Due to the degeneracy of the genetic code, many different oligonucleotide sequences can be identified which encode the extracellular domain of Sequence I.D. No. 1. Accordingly, the invention embraces oligonucleotides which encode the extracellular domain (as well as its fragments) but which have nucleotide sequences which differ from the sequences of the naturally-occurring E-cadherin gene.

In addition to the foregoing oligonucleotides, the invention also provides an isolated oligonucleotide that is capable of hybridizing under stringent conditions to the nucleotide sequence residing between position 559 and position 2224 inclusive of Sequence I.D. No. 1 (i.e., the region of the E-cadherin cDNA which encodes the extracellular domain (Sequence I.D. No. 1)). As used herein, the phrase "hybridizing under stringent conditions" is a term of art which refers to the conditions of temperature and buffer concentration which will permit hybridization of a particular oligonucleotide or nucleic acid to its complementary sequence and not to non-complementary sequences. The exact conditions which constitute "stringent" conditions, depend upon the length of the nucleic acid sequence and the frequency of occurrence of subsets of that sequence within other non-identical sequences. By varying hybridization conditions from a level of stringency at which no hybridization conditions occurs to a level at which hybridization is first observed, one of ordinary skill in the art can, without undue experimentation, determine conditions which will allow a given sequence to hybridize only with identical sequences. Suitable ranges of such stringency conditions are described in Krause, M. H. and S. A. Aaronson, Methods in Enzymology, 200:546–556 (1991). Stringent hybridization conditions, depending upon the length and commonality of a sequence, may include hybridization conditions of from 30° to 60° C. and from 5× to 0.1×SSC. Highly stringent hybridization conditions may include hybridization at 45° C. and 0.1 SSC. Less than stringent conditions are employed to isolate nucleic acid sequences which are substantially similar, allelic or homologous to any given sequence. In a particularly preferred embodiment, the isolated oligonucleotide is 100% homologous with the nucleotide sequence residing between position 559 and position 2224 inclusive of Sequence I.D. No. 1. Exemplary high stringency hybridization conditions are provided in pending U.S. patent application Ser. No. 08/199,776, the contents of which are incorporated herein by reference.

Alternatively, the isolated oligonucleotide is capable of hybridizing under stringent conditions to a unique fragment of the nucleotide sequence residing between positions 559 and 2224 of Sequence I.D. No.1. As used herein, the phrase "unique fragment" refers to a nucleic acid sequence having less than 25% sequence homology with previously identified nucleic acid sequences. More preferably, the unique fragments have less than 10% sequence homology with known nucleic acid sequences. Such unique fragments can be identified by searching the Genbank, PIR and/or Swiss-Prot data bases (e.g., release date Jan. 20, 1994) using the Eugene program available through the Harvard Molecular Biology Core Research Resource, Cambridge, Mass. The unique fragments are useful, for example, as probes and primers in nucleic acid hybridization assays and in amplification reactions, respectively.

For applications directed to the use of an isolated oligonucleotide for regulating transcription and/or translation of the extracellular domain of E-cadherin, the preferred oligonucleotide is an antisense oligonucleotide between about 10 and about 100 nucleotides in length. The antisense oligonucleotide is capable of hybridizing under high stringchoy conditions to unique fragments of the extracellular domain of Sequence I.D. No. 1. As used herein, "antisense oligonucleotide" refers to an oligonucleotide (DNA and/or RNA) that is capable of hybridizing to the naturally-occurring DNA or mRNA encoding the novel $\alpha^E$ subunit of human integrin. In a preferred embodiment, the antisense oligonucleotide is capable of hybridizing in vivo to the nucleotide sequence residing between positions 559 and 2224 inclusive of Sequence I.D. No. 1 or its transcription product. Base-pairing of the antisense oligonucleotide with the DNA (or RNA) encoding the extracellular domain of E-cadherin in vivo, prevents adhesion of the intra-epithelial lymphocytes to mucosal epithelial cells by preventing transcription (or translation) of E-cadherin in epithelial cells.

Methods for expressing the above-identified oligonucleotides in a suitable expression system including a host cell are well known to those of ordinary skill in the art (see, e.g., Sambrook, et al., *Molecular Cloning, A Laboratory Manual,* 2d ed., Cold Spring Harbor Laboratory Press, Plainview, N.Y. (1989)). The term "host cell" refers to a prokaryotic or eukaryotic cell which, together with a recombinant vector, comprises an expression system. The term host cell also embraces a host cell in which the vector or isolated oligonucleotide has integrated into the host cell nucleic acid. In a preferred embodiment, the expression vector includes at least one strand of the above-disclosed isolated oligonucleotide. Preferably, the oligonucleotide is operatively joined to at least one regulatory sequence, e.g., a promoter sequence, an enhancer sequence. A coding sequence (e.g., the isolated oligonucleotide) and a regulatory sequence are said to be operatively joined when they are linked in such a way as to place expression of the coding sequence under the influence or control of the regulatory sequence.

Suitable cell lines include mammalian cells (e.g., Chinese hamster ovary cells (CHO), monkey COS10C7 or 19 cell); bacterial cells (e.g., *E. coli, B. subtilis* and Pseudomonas strains); insect cells (e.g., SF9) and various yeast strains. Exemplary procedures for obtaining expression of a foreign gene in the above-identified cell lines are disclosed in U.S. Pat. No. 5,211,657, the entire contents of which are incorporated herein by reference.

EXAMPLES

The role of E-cadherin in modulating heterotypic adhesion between E-cadherin expressing cells (e.g., epithelial cells, endothelial cells) and T lymphocytes (e.g., intra-epithelial cells) was accomplished by: (1) developing anti-epithelial cell hybridomas; (2) screening the hybridomas for the ability to block the adhesion of intra-epithelial (but not peripheral blood) lymphocytes to 16E6.A5 epithelial cells in an adhesion assay; (3) subcloning the hybridomas of interest using limiting dilution; (4) using the hybridomas to immunoprecipitate an epithelial cell antigen; (5) biochemically characterizing the immunoprecipitated epithelial cell antigen by, for example, comparing its electrophoretic profile with that obtained by immunoprecipitating epithelial cells with an antibody specific known to be specific for E-cadherin (E4.6 mAb); and (6) indirect immunoperoxidase staining of human small intestine stained with the E4.6 mAb. Biochemical analysis demonstrated that the monoclonal antibodies which inhibited adhesion between intra-epithelial T lymphocytes and epithelial cells specifically immunoprecipitated E-cadherin. Indirect immunoperoxidase staining showed that in the submucosa, endothelial cells stain positive with the E4.6 mAb on the luminal and basolateral surfaces. Each of the above-noted steps is described in detail in the Examples.

The materials and methods relating to the identification of E-cadherin as a novel receptor for a T lymphocyte ligand are described in Example I. The regulation of expression of the $\alpha^E \beta_7$ integrin on IEL and on peripheral blood lymphocytes and the role of $\alpha^E \beta_7$ integrin in IEL adhesion to epithelial cells are described in Examples II and III, respectively. Example IV describes the production and characterization of anti-epithelial cell monoclonal antibodies that were used to define the role of E-cadherin in $\alpha^E \beta_7$ dependent cell to cell adhesion (Example V). Example VI provides a prophetic method for identifying the precise epitopes of E-cadherin that are involved in binding to heterotypic cognates of E-cadherin in T lymphocytes. Example VII illustrates an adhesion assay for selecting fucntionally equivalent peptide analogs of the extracellular domain of E-cadherin.

All references, patents and patent publications that are recited in this application are incorporated in their entirety herein by reference.

Example I

MATERIALS AND METHODS

Abbreviations

CD, cluster of differentiation; DMEM, Dulbecco's modified eagle medium; EDTA, ethylene diamine tetraacetic acid; ELAM, endothelial leukocyte adhesion molecule; FACS, fluorescence activated cell sorting; FCS, fetal calf serum; FITC, fluorescene isothiocyanate; HUVEC, human umbilical vein endothelial cells; HAT, hypoxanthine-aminopterin-thymidine; ICAM, intercellular adhesion molecule; IFN, inteferon; Ig, immunoglobulin; IL, interleukin; LN, lymph node; MHC, major histocompatibility complex; mAb, monoclonal antibody; kDa, kilodaltons; PHA, phytohemagglutinin; PAGE, polyacrylamide gel electrophoresis; SDS, sodium dodecyl sulfate; $M_r$, relative mass; LAD, leukocyte adhesion deficiency; PBL, peripheral blood lymphocyte; IEL, intestinal intra-epithelial lymphocyte(s); HML-1, human mucosal lymphocyte antigen-1; LFA-1 ($\alpha^L\beta_2$), lymphocyte associated antigen-1; TCR, T cell receptor; TBS, tris buffered saline; TNF, tumor necrosis factor; VCAM-1, vascular cell adhesion molecule-1; LPAM-1 ($\alpha^4\beta_7$), lymphocyte Peyer's patch adhesion molecule-1; TGF-$\beta$1, transforming growth factor-beta 1; MFI, mean fluorescence intensity. Human E-cadherin (Gen Bank accession #L08599) also is referred to as Uvomorulin, L-CAM, or Cell Cam 120/80.

Monoclonal Antibodies (mAbs)

Previously described mAb used were P3 (non-binding mouse control, IgG1) (Kohler G. et al. (1975) Nature (London) 256:495), OKT3 (mouse anti-human CD3, IgG2a, available from ATCC), OKT8 (mouse anti-human CD8$\alpha$, IgG2, available from ATCC), T8/2T85H7 (mouse anti-human CD8$\beta$, IgG2a) (Shiue L. et al. (1988) J. of Experimental Med. 168:1993), HML-1 (mouse anti-human ($\alpha^E\beta_7$, IgG2a) (Cerf-Bensussan N. et al. (1987) Eur. J. Immunol. 17:1279), BerACT8 (mouse anti-human ($\alpha^E\beta_7$, IgG1) (Kruschwitz M. et al. (1991) J. Clin. Path. 44:636), TS 1/18 (mouse anti-human $\beta_2$, IgG1) (Sanchez-Madrid F. et al. (1983) J. Exp. Med 158:1785), TS 1/22 (mouse anti-human $\alpha^L$, IgG1) (Sanchez-Madrid F. et al. (1982) Proc Nat Acad Sci USA 79:7489), A-1A5 (mouse anti-human $\beta_1$, IgG2b) (Hemler M. E. et al. (1983) J. of Immunol. 131(1):334), 4B4 (mouse anti-human $\beta_1$, IgG1) (Morimoto C. et al. (1985) J. of Immunol. 134(6):3762) TS 2/7 (mouse anti-human $\alpha^1$, IgG1) (Hemler M.E. et al. (1985) J. Biol. Chem. 260(28):15246), 12F1 (mouse anti-human $\alpha^2$, IgG2a) (Pischel K. et al. (1987) J. Immunol 138:226), J143 (mouse anti-human ($\alpha^3$, IgG1) (Fradet Y. et al. (1984) Proc. Natl. Acad. Sci. 81:224), B-5G10 (mouse anti-human ($\alpha^4$, IgG1) (Hemler M. E. et al. (1987) J. Biol. Chem. 262:11478), HP ½ (mouse anti-human $\alpha^4$) (Sanchez-Madrid F. et al. (1986) Eur. J. of Immunol. 16(11):1343) BIE5 (rat anti-human $\alpha^5$) (Werb Z. et al. (1989) J. of Cell Biol. 109:877), GOH3 (rat anti-human-$\alpha^6$) (Sonnenberg A. et al. (1987) J. of Biol. Chem. 262(21):10376), TS 2/18 (mouse anti-human CD2, IgG1) (Sanchez-Madrid F. et al. (1982) Proc Natl Acad Sci USA 79:7489), W6/32 (mouse anti-human MHC class I, IgG2a) (Barnstable, C. et al. (1978) Cell 14(1):9), BB7.7 (mouse anti-human MHC class I, IgG2b) (Brodsky F. et al. (1979) Immunol. Rev. 47:3), HECD-1 (mouse anti-human E-cadherin, IgG1, available from ZYMED, San Francisco, CA), ECCD-2 (rat anti-mouse E-cadherin, cross reacts with human E-cadherin, IgG1, available from ZYMED, San Francisco, Calif.), DECMA-1 (rat anti-mouse E-cadherin, cross reacts with human E-cadherin, IgG1, available from Sigma, St. Louis, Mass.), 187.1 (rat anti-mouse k light chain)(Yelton D. et al. (1981) Hybridoma 1:5) and Y-3 (mouse anti-mouse H-2 $K^b$) (Jones B. et al. (1981) Nature 292(5823):547). While the exact specificities of HML-1, BerACT8, E/7-1 and E/7-2 have not been defined, all immunoprecipitate a heterodimer composed of 175 and 105 kDa species, designated $\alpha^E$ and $\beta_7$ respectively. In addition they do not recognize the $\alpha^4\beta_7$ complex, and are thus likely to be either $\alpha$ chain specific or recognize a combinatorial epitope of $\alpha^E\beta_7$. mAb cross-blocking studies revealed that HML-1 and BerAct8 recognize the same or overlapping epitopes.

Generation of new mAbs

Development of $\alpha^L\beta_2$ hybridoma. To produce the D6.21 mAb (IgG2a), a Balb/c female mouse immunized intraperitoneally four times at two week intervals with 1×10$^7$ Jurkat cells in 0.5 ml PBS, and then intravenously with 5× 10$^6$ Jurkat cells in 0.25 ml PBS. Three days following the intravenous immunization, the spleen was harvested and fused with the P3X63Ag8.653 myeloma cell line at a ratio of 10 spleen cells per myeloma cell. Hybridomas were grown with MRC-5 fibroblast feeders in RPMI 1640 with 20% FCS, 10 mM HEPES, 2 mM L-glutamine, 100 units/ml penicillin, and 100 µg/ml strepmmycin sulfate, and 50 µM 2-mercaptoethanol in 5% CO$_2$. HAT selection (Boehringer Mannheim, Indianapolis, Ind.) was begun 24 hrs. after the fusion. Antibodies were screened for the ability to block cytotoxic T-lymphocyte mediated lysis of $^{51}$Cr labeled target cells. D6.21 was cloned by limiting dilution and isotyped by ELISA using affinity purified antibodies to mouse immunoglobulins (Zymed Immunochemicals, San Francisco, Calif.). Analysis of a panel of cell lines by FACS revealed that staining with the D6.21 mAb was indistinguishable from that seen with the defined anti-LFA-1 mAb TS 1/18 and TS 1/22. In addition, the D6.21 mAb immunoprecipitates a complex indistinguishable from the $\alpha^L\beta_2$ integrin heterodimer.

Development of anti-epithelial cell hybridomas. 16E6.A5 cell monolayers were disrupted with 5 mM EDTA in PBS and the resulting suspension was washed three times with PBS. 1×10$^8$ 16E6.A5 cells in 0.5 ml PBS were used to intraperitoneally immunize Rbf/DnJ mice (Jackson Labs, Bar Harbor, Me.) three times at two week intervals. 5×10$^7$ cells were lysed in sterile 0.1% TX-100, TBS rocking at 4° C. for 1 hr. in a final volume of 500 µl in an eppendorf tube. Insoluble material was removed by centrifugation in a microfuge for 20 min. Supernatant was collected and centrifuged a second time for 20 min. Cleared supernatant was diluted 1:1 with sterile PBS. Three days prior to the fusion, 0.3 ml of cleared, diluted 16E6.A5 lysate was injected IV and 5×10$^7$ 16E6.A5 cells in PBS were injected IP (intraperitoneally) as an antigenic boost. Spleen cells were fused to P3X63Ag8.653 myeloma cells in serum free media at a ratio of 4:1 with 50% PEG 1500 in HEPES (Boehringer Mannheim, Indianapolis, Ind.). Hybridomas were grown with Va2 fibroblast feeders (SV-40 transformed fibroblast cell line, obtained from Vimla Band, New England Medical Center) in DMEM, high glucose with 20% CPSR-3 (serum replacement, Sigma, St. Louis, Mo.), 5% hybridoma enhancing supplement (Sigma, St. Louis, Mo.), 10 mM HEPES, 2 mM L-glutamine, 100 units/ml penicillin, and 100 µg/ml streptomycin sulfate, 10 µg/ml gentamycin, and 50 µM 2-mercaptoethanol in 10% CO$_2$. HAT selection (Boehringer Mannheim, Indianapolis, Ind.) was begun 24 hrs. after the fusion. Antibodies were screened for the ability to block the adhesion of IEL to 16E6.A5 epithelial cells. Hybridomas of interest were subcloned using limiting dilution and isotyped by ELISA using immobilized anti-mouse Ig (Amersham, UK).

Cell culture

Human intestinal tissue was obtained from fatal accident organ donors or from adult patients undergoing resection for colorectal carcinoma, from sections at least 10 cm away from macroscopically detectable lesions. IEL were isolated as described previously (Davies M. D. J. et al. (1981) Gut 22:481; Parker C. et al. (1992) Proc. Natl. Acad. Sci. USA 89:1924). Once isolated, the IEL were stimulated with phytohemagglutinin-P (PHA:Difco) and irradiated feeder cells (80% peripheral blood mononuclear cells and 20% JY lymphoblastoid cells) in Yssel's medium (Yssel H. et al. (1984) J. Immunol. Methods 72:219) containing 2 nM recombinant interleukin (IL)-2 (gift of Ajinomoto, Kawasaki, Japan), 4% (vol/vol) conditioned medium (Brenner M. et al. (1987) J. Immunol. 138:1502), 4% (vol/vol) fetal calf serum (Hyclone), and 50 µM 2-mercaptoethanol at 10% $CO_2$. In two-color FACS analysis, the majority of the $CD3^+$ cells examined expressed an $\alpha\beta$ TCR, were $CD8^+$, HML-$I^+$, and had a cell surface phenotype that included IL-$2R^+$ (p55), integrin $\alpha^{1+}$ and $CD45RO^+$ consistent with an activated state. Two different anti-CD8 mAb (OKT8, CD8$\alpha$; and T8/2T85H7, CD8$\beta$) were used to discriminate between expression of the CD8 $\alpha\alpha$ homodimer and the CD8 $\alpha\beta$ heterodimer. In agreement with previously reported data (Jarry A. et al. (1990) Eur. J. of Immunol. 20(5):1097), 10% of the $CD8^+$ cells expressed the homodimer. Thus, the lines were thought to be highly purified IEL preparations. Long term culture of the 032891 and 3901 IEL lines was maintained by intermittent restimulation with PHA and irradiated feeder cells. In single color FACS analysis, the long term 032891 cell line was 99% $CD3^+$, 99% T cell receptor $\alpha\beta$ positive, and 99% CD8 $\alpha\beta$ positive. The 390I cell line was 99% $CD3^+$, 99% T cell receptor $\alpha\beta$ positive, and 99% CD8 $\alpha\beta$ positive and 6% CD4 positive. For cytokine treatment, IEL were grown in 2 ng/ml TGF-$\beta$1 (gift of Celtrix, Palo Alto, Calif.) for 4–25 days.

PHA blasts were derived by stimulating mononuclear cells from peripheral blood with phytohemagglutinin-P (PHA:Difco) and irradiated feeder cells (80% peripheral blood mononuclear cells and 20% JY lymphoblastoid cells) in Yssel's medium (Yssel H. et al. (1984) J. Immunol. Methods 72:219) containing 2 nM recombinant interleukin (IL)-2 (gift of Ajinomoto, Kawasaki, Japan), 4% (vol/vol) fetal calf serum (Hyclone), and 50 µM 2-mercaptoethanol and grown in 10% $CO_2$. Mononuclear cells were isolated with Ficoll-Hypaque (Pharmacia Chemicals, Uppsasa, Sweden).

The breast epithelial cell line 16E6.A5 (provided by Dr. V. Band, Tufts Univ., New England Medical Center, Boston, Mass.) was derived by immortalization of the 76N normal epithelial cell line through transfection of the E6 and E7 genes of the human papilloma virus (Band V. et al. (1989) Proc. Natl. Acad. Sci. 86:1249; Band V. et al. (1990) Proc. Natl. Acad. Sci. 87:463). Immortalized cells were selected by growth in DFCI-2 medium (Band V. et al. (1991) J. of Virology 65:6671). 16E6.A5 is one of the clones obtained from pooled populations of immortalized cells. It was grown in DFCI-1 medium which consists of $\alpha$-MEM/HAM nutrient mixture F12 (1:1, vol/vol) (Gibco) supplemented with 12.5 ng/ml epidermal growth factor, 10 nM triiodothyronine, 10mm HEPES, 50 µM freshly dissolved ascorbic acid, 2 nM $\beta$-estradiol, 1 µg/ml insulin, 2.8 µM hydrocortisone, 0.1 mM ethanolamine, 0.1 mM phosphoethanolamine, 10 µg/ml transfertin, 2 mM L-glutamine, 100 units/ml penicillin, and 100 µg/ml streptomycin sulfate, 15 nM sodium selenite (all from Sigma); 1 ng/ml cholera toxin (Schwartz/Mann); 1% (vol/vol) fetal bovine serum (Hyclone); and 35 µg/ml bovine pituitary extract (Hammond Cell/Tech, Alameda, Calif.) at 5% $CO_2$. Confluent monolayers of 16E6.A5 cells were subcultured by incubation with a 0.025% trypsin/0.01% EDTA (Sigma) solution for 9 min. at 37° C. Trypsin digestion was stopped with 0.0375% trypsin inhibitor (Sigma) in PBS.

The T84 colon carcinoma cell line was obtained from ATCC and grown in DMEM/HAM nutrient mixture F12 (1:1, vol/vol) (Gibco) supplemented with 15 mM HEPES, 1.2 g/liter $NaHCO_3$, 40 mg/liter penicillin, 8 mg/liter ampicillin, 90 mg/liter streptomycin sulfate, and 5% (vol/vol) fetal calf serum (Hyclone). Confluent monolayers of T84 cells were subcultured by incubation with a 0.1% trypsin/0.9 mM EDTA solution in phosphate buffered saline for 20 min. at 37° C.

Human umbilical vein endothelial cells (HUVEC, obtained from William Atkinson, Brigham and Women's Hospital, Boston, Mass.) were grown on plastic coated with 0.1% gelatin in PBS in M199 media (Gibco) supplemented with 2 mM L-glutamine, 100 units/ml penicillin, and 100 µg/ml streptomycin sulfate, 10% (vol/vol) fetal bovine serum (Hyclone), 10 mM HEPES, 30 µg/ml endothelial cell growth factor (Collaborative Research), and 100 U/ml heparin. Confluent monolayers of HUVEC cells were subcultured by incubation with a 0.05% trypsin/0.53 mM EDTA solution in phosphate buffered saline for 4 min. at 25° C. The second passage of HUVEC was plated in 96-well plates and allowed to reach confluence for use as a substrate in adhesion assays. HUVEC monolayers used in adhesion assays were cultured with 20 ng/ml rIL-1$\beta$ (gift of DuPont through the Biological Response Modifiers Program, National Cancer Institute) for 8.5 hours.

The murine fibroblast cell line L-M (ATCC CCL1.3) and the human fibroblast cell line Va2 (obtained from Vimla Band, New England Medical Center, Boston, Mass.) were grown in DMEM, high glucose with 10% bovine calf serum (Hyclone), 10 mM HEPES, 2 mM L-glutamine, 1 mM sodium pyruvate, 10 µm non-essential amino acids (Gibco), 100 units/ml penicillin, and 100 µg/ml streptomycin sulfate, and 50 µM 2-mercaptoethanol in 10% $CO_2$. L-M transfectants were grown in the above media with G418 (Gibco) at 500 µg/ml.

The B lymphoblastoid cell line, JY, the human epidermoid carcinoma, A431 (ATCC CRL 1555), and the fibroblast cell line, MRC5, were grown in RPMI 1640 with 10% bovine calf serum (Hyclone), 10 mM HEPES, 2 mM L-glutamine, 100 units/ml penicillin, and 100 µg/ml streptomycin sulfate, and 50 µM 2-mercaptoethanol in 5% $CO_2$.

COS-7 cells were grown in DMEM, high glucose with 10% Nu-Serum (Collaborative Research, Inc., Bedford, Mass.), 1 mM sodium pyruvate, 10 mM HEPES, 2 mM L-glutamine, 100 units/ml penicillin, and 100 µg/ml streptomycin sulfate, and 50 µM 2-mercaptoethanol in 10% $CO_2$.

Mammalian Cell Transfection

Production of stable transfectants. E-cadherin in the pERF-1 vector (containing a CMV promoter) and the pERF-1 vector alone were transfected into L-M cells using the $CaPO_4$ method (C. Chen and H. Okayama, Molecular and Cellular Biol. 7:2745–2752 (1987)). 20 hrs. prior to transfection, $1\times10_6$ exponentially growing L-M cells were plated in a 100 mm tissue culture dish. 30 µg of plasmid DNA was diluted to 450 μl in sterile RO water and 50 μl of 2.5M $CaCl_2$ was added. Next, 500 μl of N,N-bis(2-hydroxyethyl)-2-aminoethanesulfuric acid in buffered saline, pH 6.95 was added and the mixture was vortexed and allowed to sit at room temperature for 10 min. while a precipitate formed. The suspension was added dropwise to cells at 40% confluence in 10 ml media and the cells were incubated in 5% $CO_2$ for 20 hours. The suspension was removed and the cells were washed twice in PBS before being cultured in complete media for 20 hrs. in 10% $CO_2$. 40 hrs. post transfection, the cells were harvested with trypsin-EDTA and split 1:10 and 64 hours post transfection selection with 500 μg/ml G418 was applied. G418 resistant colonies were visible on day 14.

Magnetic Bead Selection. G418 resistant L-M cells expressing E-cadherin were isolated by positive selection with magnetic beads. L-M monolayers expressing the transfected gene were washed with Hank's buffer containing 1 mM $CaCl_2$ (to maintain E-cadherin expression) and incubated with 0.01% trypsin in Hank's buffer containing 1 mM $CaCl_2$ at 37° C. for 3 min. Trypsin activity was stopped with 0.0375% trypsin inhibitor in Hank's buffer containing 1 mM $CaCl_2$. $4 \times 10^7$ cells were resuspended in 4 ml of RPMI containing 10% bovine calf serum, 2% human serum, 10 mM HEPES, 1 mM $CaCl_2$, and a 1/100 dilution of E4.6 ascites and incubated at 4° C. for 90 min. Unbound antibody was washed off and pre-washed magnetic beads (Dynabeads, goat anti-mouse, P & S Biochemicals, Gaithersburg, Md.) were added at a ratio of 2 cells/bead. L-M cells were incubated with the magnetic beads while rocking for 15 min. at 4° C. Cells attached to beads were collected with a magnet and unbound cells were removed by washing five times and aspirating the supernatant. L-M cells positive for E-cadherin were detached from the magnetic beads through incubation in the presence of 1 mM EDTA. Beads were collected with a magnet and the supernatant containing the positively selected cells was harvested and returned to culture.

Fluorescence-Activated Cell Sorting. L-M cells expressing high levels of E-cadherin were isolated by FACS sorting. L-M cells were harvested in the presence of 1 mM $CaCl_2$ as described for magnetic bead selection and incubated with the E4.6 mAb, washed and then incubated with the secondary mAb, FITC-conjugated goat anti-mouse $F(ab')_2$. The brightest 1–10% of E-cadherin expressing L-M cells were collected using a FACSort (Becton-Dickenson). Several rounds of sorting were necessary to increase the mean fluorescence intensity from 20 to 200.

Production of transient transfectants. COS-7 cells were transiently transfected with the expression vector Ap$^r$M8 containing, integrins $\alpha^E$, $\alpha^4$, and $\beta_7$ in various combinations as well as $\beta_7$ in the reverse orientation. Exponentially growing cells were plated at 30% confluence 20–24 hours prior to transfection. 2 μg of each DNA was diluted in 3 ml complete media containing 400 μg/ml DEAE-dextran and 100 μM chloroquine phosphate. Media was aspirated from the COS-7 cells, the DNA mixture was added, and the cells were incubated at 37° C. in 10% $CO_2$ for 3.5 hrs. Next, the cells were incubated in PBS containing 10% DMSO for 2 min. at room temperature, washed in PBS and incubated in complete media. After 24 hrs. the media was replaced, at 48 hrs. the COS-7 cells were split 1:2 and at 72 hours, they were analyzed.

Fluorescence-Activated Cell Sorter Analysis (FACS)

FACS analysis was performed by suspending $2.5 \times 10^5$ cells in 100 μl of staining buffer (PBS, 1% BSA, 4% human serum, 0.02% $NAN_3$) containing saturating concentrations of mAbs and incubating for 1 hr. at 4° C. After three washes with staining buffer, cells were resuspended in staining buffer containing the secondary mAb FITC-conjugated $F(ab')_2$ goat anti-mouse or goat anti-rat Ig (Tago Inc., Burlingame, Calif.) at saturating concentrations. After 1 hr. at 4° C., unbound antibody was removed and cells were resuspended in staining buffer containing 1.25 μg/ml propidium iodide. In order to perform two color analysis, cells were first stained with unconjugated mAbs followed by FITC-conjugated goat anti-mouse Ig. Cells were then incubated with saturating amounts of normal mouse serum to block residual goat anti-mouse binding sites. Biotin-conjugated mAbs were used to stain the second molecule which was visualized by PE-conjugated streptavidin (Becton Dickinson & Co., Mountain View, Calif.). Viable cells were analyzed using the FACScan or FACSort flow cytometer (Becton Dickinson & Co.).

Adhesion Assays

Monolayers of adherent cells were grown in flat bottomed 96-well Linbro tissue culture plates. $10^4$ adherent cells in 100 μl complete media were added per well and allowed to grow for two to three days until they reached confluence. Just prior to the addition of IEL or transfected COS 7 cells, the adherent cell monolayers were washed with assay media. To label IEL and COS-7 cells, 25 μg of 2',7'-bis-(2-carboxyethyl)-5 (and -6)-carboxyfluorescein (BCECF-AM, Molecular Probes, Inc., Eugene, Oreg.) was diluted in 5 μl DMSO and added to a suspension of $5 \times 10^6$/ml IEL or COS-7 cells in complete media. The cells were incubated at 37° C. for 25 minutes then washed twice in assay media (PBS containing 1 mM $CaCl_2$, 2 mM $MgCl_2$ and 10 mM HEPES). After washing, 50,000 labeled IEL or COS-7 cells in 100 μl of assay media were added to the adherent cell monolayers. IEL or COS-7 cells were allowed to settle onto adherent cell monolayers for 25 or 40 min. at 37° C. Unbound cells were removed by flicking media from the plate. Bound cells were detected using a Fluorescence plate reader (IDEXX Co., Portland, Me.). If antibody blocking was performed, the IEL, COS-7 cells, epithelial cell monolayers, or L-M monolayers were pre-incubated with a 1:250 dilution of ascites fluid or 10 μg/ml of purified mAb for live minutes at 37° C. prior to encounter with the second cell type. At least four replicates were performed. The % cells bound was calculated by reading the fluorescence units obtained after unbound cells were washed off, dividing this number by the input fluorescence units and multiplying by 100. Serial dilutions of labeled cells showed that as few as 1000 cells were detected in the linear range.

In adhesion assays where divalent cations were varied, the IEL were washed with $Ca^{++}$ and $Mg^{++}$ free Hank's balanced salt solution (HBSS) and pre-equilibrated with HBSS containing the indicated concentrations of $MgCl_2$, $MnCl_2$, or $CaCl_2$ for 10 min. at 37° C. prior to incubation with 16E6.A5 monolayers which had been washed with $Ca^{++}$ and $Mg^{++}$ free HBSS.

Disruption of T84 cell intercellular tight junctions

Confluent monolayers of T84 cells in 96-well plates were incubated with 1 mM EDTA for 20 min. at 37° C. and washed with assay medium prior to use as a substrate in adhesion assays. To verify that tight junctions were disrupted by these conditions, filter grown monolayers of T84 cells were treated with 1 mM EDTA for 20 min., and the ability of the T84 cell monolayer to resist the passage of electrical current placed across the monolayer was assessed using previously detailed electrical assays (Dharmsathaphorn K. et al. (1990) Methods in Enzymology 192:354). Depletion of $Ca^{++}$ with 1 mM EDTA elicited a tall in transepithelial resistance to passive ion flow (461.1±58.7 vs. 56.8±3.5 ohm×cm$^{-2}$ for baseline vs. Ca$^{++}$ depleted states respectively). Upon Ca$^{++}$ repletion, the resistance remained low for greater than 25 min. (76.6±3.3 ohm×cm$^{-2}$ at 59 min.) demonstrating that the junctions were open for the duration of an adhesion assay.

Coculture of T84 epithelial cells with IEL and staining of monolayers for confocal microscopy Confluent monolayers of T84 cells were trypsinized and resuspended at 1×10$^6$/ml in T84 cell medium containing 1 nM rIL-2 and equal numbers of IEL which had been grown in TGF-β1 for at least 5 days. 1 ml of this suspension was plated on top of sterile coverslips in 24-well plates. After culture for 7 days, the cells were fixed with 3.7% paraformaldehyde for 20 min., washed with PBS containing 0.2% gelatin, extracted with acetone at −20° C. for 5 min., and air dried. Next, the monolayers were rehydrated with PBS, incubated with 50 mM NH$_3$Cl, and washed with PBS containing 0.2% gelatin. Then, the monolayers were incubated with 10% goat serum and incubated with OKT8 at a 1:100 dilution of ascites for 90 min. FITC conjugated goat anti-mouse Ig was used as a second step reagent. Finally, monolayers were incubated with rhodamine-conjugated phalloidin for 30 min. to stain f-actin. Coverslips were mounted on cleaned glass slides with p-phenylenediamine, and the fluorescent staining was visualized using confocal microscopy.

Immunohistochemistry

Tissue samples were mounted in OCT (Ames Co., Elkart, Ind.), frozen in liquid nitrogen and stored at −70° C. Frozen tissues were cut into 4 μm thick sections, fixed in acetone for 5 min., air dried, and stained with mAbs. Detection of staining was carried out with an indirect immunoperoxidase technique (Cerf-Bensussan N. et al. (1984) J. of Immunol. 132:2244) using avidin-biotin-peroxidase (Vector Laboratories, Burlingame, Calif.) and 3-amino-9-ethylcarbazole (Aldrich Chemical Co. Inc., Milwaukee, Wis.) as the chromogen.

Labeling and Immunoprecipitation

Surface Labeling. Cultured IEL (2×10$^7$) isolated by centrifugation with Ficoll-Hypaque (Pharmacia Chemicals, Uppsasa, Sweden) were surface labeled with 1 mCi Na$^{125}$I (Du Pont-New England Nuclear, Boston, Mass.) using lactoperoxidase and hydrogen peroxide in 0.5 ml of PBS on ice as previously described (Brenner M. et al. (1987)J. Immunol. 138:1502). Adherent cells were labeled in T25 tissue culture flasks in 1.5 ml using the same reaction. The cells were solubilized in lysis buffer containing Tris Buffered Saline (TBS, 50 mM Tris-Base, pH 7.6, 140 mM NaCl) with 0.5% Triton X-100 or 1% (wt/vol) digitonin, 8 mM iodoacetamide (IAA) and 1 mM phenylmethylsulfonyl fluoride (PMSF, Sigma, St. Louis, Mo.) for 1 hr at 4° C. Detergent insoluble material was removed by centrifugation for 10 min. in a microfuge at 4° C. The supernatant was precleared with 4 μl normal rabbit serum and 400 μl 187.1 mAb as culture supernatant for 30 min. followed by two rounds (1 hr. and 12 hrs.) of 200 μl of a 10% (wt/vol) cell suspension of fixed Staphlococcus aureus Cowen strain I (PANSORBIN, Calbiochem, San Diego, Calif.). Lysates containing the equivalent of 1–2×10$^6$ cells were immunoprecipitated with 0.1–5 μl of ascites or 50–200 μl of culture supernatant. All IgG1 mAbs were used in combination with rat anti-mouse kappa chain mAb, 187.1, culture supernatant for optimal protein A binding. Immune complexes were then incubated with protein A-Sepharose (Pharmacia LKB Biotechnology Inc., Piscataway, N.J.) for 1 hr. at 4° C. with rocking. The immunoprecipitates were washed five times with 0.1% (vol/vol) Triton X-100 containing TBS, eluted with sample buffer (10% glycerol, 3% SDS, 0.5M Tris, pH 6.8) and analyzed by SDS-PAGE as described (Laemmli U. (1970) Nature 227(259):680).

Metabolic Labeling. Exponentially growing, 85–90% confluent, 16E6.A5 cells were incubated with 2.5 ml of methionine-and cysteine-free RPMI 1640 (Select-Amine kit, Gibco Laboratories, Grand Island, N.Y.) supplemented with 10% dialyzed fetal calf serum and 20 mM HEPES, pH 7.4 (labeling media) for 20 min. at 37° C. in a T25 tissue culture flask. Next, 1 mCi of [$^{35}$S] methionine and [$^{35}$S] cysteine (EXPRE$^\pm$S$^\pm$S Du Pont-New England Nuclear, Boston, Mass.) was added and the cells were labeled for 4 hours. The cells were then washed in ice-cold PBS and solubilized in lysis buffer containing 1% Triton X-100. Preclearing and immunoprecipitations were performed as described above. Precipitated material was separated on SDS-PAGE and visualized with standard fluorographic procedures (Bonner W. et al. (1974) Eur. J. of Biochem. 46(1):83). For pulse chase experiments, 16E6.A5 cells were grown to 90% confluence in wells of a 24 well plate (Linbro, Flow Laboratories, McLean, Va.) and incubated with 0.3 ml labeling media for 20 min. at 37° C. prior to the addition of 0.08 mCi of [$^{35}$S] methionine and [$^{35}$S] cysteine (EXPRE$^{35}$S$^{35}$S Du Pont-New England Nuclear, Boston, Mass.) for 15 min. The cells were then washed in ice-cold PBS and incubated at 37° C. in DFCI-1 media without radiolabel for 0 min., 15 min., 30 min., 60 min., 4 hrs., or 8 hrs. before being solubilized in lysis buffer containing 1% Triton X-100. Preclearing for each time point was carried out as described above with 0.25 μl of TCRδ1 ascites and 50 μl of 187.1 culture supernatant. Specific precipitation was performed with 100 μl of E4.6 culture supernatant and 70 μl of 187.1 culture supernatant. Immunoprecipitates were separated by SDS-PAGE in a 7% gel and visualized with standard fluorographic procedures (Bonner W. et al. (1974) Eur. J. of Biochem. 46(1):83).

Two-Dimensional Iso-electric focusing (IEF)ISDS-PAGE Analysis. Exponentially growing 16E6.A5 cells at 90% confluence in a T75 tissue culture flask were surface labeled as described above in a 3 ml reaction with 2 mCi$^{125}$I and treated with neuraminidase (Gibco; 166 international units/ml) at room temperature for 1 hr. in PBS containing 0.1% bovine serum albumin, 1 mM CaCl$_2$ and 1 mg/ml glucose. The cells were then solubilized in lysis buffer containing 1% Triton X-100, and precleared and immunoprecipitated as described above. The samples were eluted in 9.33M urea, 2.5% Triton X-100, 5% 2-mercaptoethanol, and 2% ampholines pH 3.5–10 and resolved in the first dimension by IEF. The first dimensional gel was equilibrated in 23 mM Tris, pH 6.8, 10% glycerol, 2.5% SDS and 5% 2-mercaptoethanol and run in the second dimension on a 7% polyacrylamide gel in SDS-PAGE.

Peptide Mapping. 16E6.A5 cells were metabolically labeled for 15 min. as described above, chased for 0 min. or 4 hrs. Next, the cells were lysed, precleared and precipitated and the immunoprecipitates were resolved on a 7% polyacrylamide gel by SDS-PAGE. The wet gel was autoradiographed at 4° C. for 3 days and areas of the gel containing proteins of interest were excised. The gel pieces were loaded into 4 cm wide wells of a 5 cm long stacking gel in 250 μl of sample buffer containing 0.05 μg/ml V8 protease (ICN Immunobiologicals, Lisle, Ill.) and peptides were resolved on a 12% polyacrylamide gel. Samples were run two-thirds of the way into the stacking gel and the current was turned off for 30 min. to allow digestion of proteins which were then resolved by SDS-PAGE. Fluorography was carried out with standard procedures (Bonner W. et al. (1974) Eur. J. of Biochem. 46(1):83).

Endoglycosidase Digestion. N-glycanase digestion was carried out to remove mature, complex type N-glycans. Proteins were eluted from protein A-Sepharose beads by boiling for 3 min. in 60 µl of 0.5% (wt/vol) SDS and 0.1M 2-mercaptoethanol. The sample was divided in two and to each tube, 24 µl of 0.5M sodium phosphate buffer (pH 8.6) and 10 µl of 10% NP40 was added. One sample also received 2 µl of N-glycanase enzyme (250 U/ml, peptide-N[N-acetyl-β-glucosaminyllasparagine amidase; Genzyme Corporation, Boston, Mass.). Each sample was then incubated for 16 hrs. at 37° C., and analyzed by SDS-PAGE as described (Laemmli U. (1970) Nature 227(259):680).

Purification of E-cadherin-expressing cells with anti-mouse Ig-conjugated magnetic beads The E4.6 monoclonal antibody is allowed to bind to E-cadherin on the cell surface. Thereafter, the cells are incubated with anti-mouse Ig-conjugated magnetic beads for 20 min. at 4° C. Cells expressing E-cadherin bind to the beads and a magnet is used to separate these cells from cells which do not express E-cadherin. To isolate E-cadherin-expressing cells from the magnetic beads, 1 mM EDTA is added for 10 min. at room temperature or until the cells separate from the beads. The E-cadherin positive cells then are returned to culture.

Example II

Regulation of Expression of $\alpha^E\beta_7$ on Intraepithelial Lymphocytes (IEL) and Peripheral Blood Lymphocytes (PBL)

FACS analysis revealed that freshly isolated IEL express a profile of integrins that is distinctly different from that observed on peripheral blood T lymphocytes. Freshly isolated IEL expressed high levels of $\alpha^E\beta_7$ and intermediate levels of $\alpha^1$, integrins which are not expressed on freshly isolated peripheral blood T lymphocytes. In contrast, IEL expressed comparatively lower levels of $\alpha^L\beta_2$ and $\alpha^3$, $\alpha^5$, and $\alpha^6$. These differences suggest that IEL might use a different combination of adhesive interactions than peripheral blood T lymphocytes. Cultured IEL expressed lower levels of $\alpha^E\beta_7$ and higher levels of $\alpha^L\beta_2$ than freshly isolated IEL, more like peripheral blood T lymphocytes. Interestingly, it was possible to shift the integrin profile toward that expressed by freshly isolated IEL through the culture of IEL lines with TGF-β1. These conditions dramatically up-regulated expression of $\alpha^E\beta_7$, down regulated expression of $\alpha^L\beta_2$ and had little effect on the expression of $\beta_1$ and its associated α chains. These TGF-β1 mediated changes in integrin expression may be cell type specific as surface levels of members of the $\beta_1$ subfamily are up-regulated in thymocytes (Ignotz R. et al. (1987) Cell 51:189) and expression of $\alpha^L\beta_2$ is up-regulated in a human monocytic cell line by culture with TGF-β1 (Ignotz R. et al. (1989) J. Biol. Chem. 264(1):389).

Expression of $\alpha^E\beta_7$ in vivo is high (greater then 95%) on T lymphocytes located at mucosal epithelial sites such as intestine and breast and moderate (~40%) in the intestinal lamina propria, but low on PBL T cells (~2%) (Cerf-Bensussan N. et al. (1987) Eur. J. Immunol. 17:1279). The mechanism which mediates this tissue specific expression is unknown. The results presented here describing the effect of TGF-β1 on surface expression of $\alpha^E\beta_7$ suggests that tissue specific expression is mediated by the presence of TGF-β1 in the local environment. Intestinal epithelial cells in vivo are thought to produce TGF-β1 as mRNA has been isolated and immunohistochemistry reveals the presence of TGF-β1 protein (Barnard J. et al. (1989) Proc. Natl. Acad. Sci. USA 86:1578; Barnard J. et al. (1993) Gastroenterology 105(1):67; Koyama S. et al. (1989) J. of Clin. Investiga. 83(5):1768). TGF-β1 functions at this site to regulate epithelial cell proliferation and differentiation, stimulate extracellular matrix production, and modulate cell migration (Massague J. (1990) Annu. Rev. Cell Biol. 6:597). Proof that active TGF-β1 exists at this site is difficult to obtain as TGF-β1 is produced in a latent, acid-inducible form. Coculture experiments combining IEL and epithelial cells increases expression of $\alpha^E\beta_7$ on IEL suggesting that cultured epithelial cells produce active TGF-β1 which alters IEL integrin expression. As T lymphocytes can also produce TGF-β1, it is possible that the activation induced increase in $\alpha^E\beta_7$ expression as well as the increase seen on IEL cultured in the presence of 10% conditioned media may be due to TGF-β1 (Barnard J. et al. (1993) Gastroenterology 105(1):67). The ability of TGF-β1 to down-regulate expression of $\alpha^L\beta_2$ may be a mechanism by which exposure to a cytokine in a tissue-specific manner shifts the profile of integrins expressed from one which functions in general adhesive interactions in all locations to one specific to a particular tissue. Analysis of the changes in cell surface phenotype of cultured IEL mediated by TGF-β1 combined with the knowledge that TGF-β1 is produced by intestinal epithelial cells leads to the hypothesis that exposure of IEL to TGF-β1 at mucosal epithelial sites in vivo induces changes in the cell surface profile of adhesion molecules, which in turn mediate the tissue specific localization exhibited by the IEL subset of T lymphocytes. The possible induction of $\alpha^E\beta_7$ on IEL at or near the intestinal epithelium suggests that $\alpha^E\beta_7$ may mediate retention of IEL at this site. As 2% of PBL express $\alpha^E\beta_7$, it is believed that $\alpha^E\beta_7$ interacts with a receptor (E-cadherin) on endothelial cells, thereby mediating restricted recirculation of these cells to tissues expressing the receptor.

Example III

Role of $\alpha^E\beta_7$ in IEL Adhesion to Epithelial Cells

As IEL are a subset of T lymphocytes located at the basolateral surface of intestinal epithelial cells in vivo, we hypothesized that these two cell types interact and that this interaction is mediated by the $\alpha^E\beta_7$ integrin. IEL lines cultured in vitro with TGF-β1 express a similar profile of adhesion molecules to their in vivo counter-parts (Example II) suggesting that they might have similar adhesive properties. Indeed, cultured IEL lines adhered to confluent monolayers of mucosal epithelial cells in cell-to-cell adhesion assays. The binding was up-regulated by the presence of divalent cations in the medium.

We found that the integrins with the highest levels of expression on the surface of these IEL, $\alpha^E\beta_7$ and $\alpha^L\beta_2$, both played a role in IEL-epithelial cell adhesion. The relative contribution of each of these integrins to the overall IEL-epithelial cell binding was dependent on their level of surface expression. IEL expressing low levels of $\alpha^E\beta_7$ and high levels of $\alpha^L\beta_2$ were principally dependent on $\alpha^L\beta_2$ for adherence to epithelial cells. Conversely, the adhesion of IEL expressing high levels of $\alpha^E\beta_7$ and low levels of $\alpha^L\beta_2$ to epithelial cells was predominantly mediated by $\alpha^E\beta_7$. As freshly isolated IEL express high levels of $\alpha^E\beta_7$, this integrin may function in IEL-to-epithelial cell adhesion in vivo. It is possible that both $\alpha^E\beta_7$ and $\alpha^L\beta_2$ contribute to IEL-to-epithelial cell binding even in conditions when one of these integrins predominates. This is suggested by the finding that blocking with a combination of antibodies specific for $\alpha^E\beta_7$ and $\alpha^L\beta_2$ was more effective than either one alone. This marked double blocking suggested that these two integrins together were the predominant mediators of IEL-epithelial cell binding.

IEL and epithelial cells produce cytokines which modulate their own proliferation and differentiation or effector function; however, once secreted, these cytokines effect any responsive cell in the vicinity. IEL-to-epithelial cell adhesion was modulated by IFN-γ which increased adhesion. As IFN-γ is known to increase ICAM-1 expression (Dustin M. L. et al. (1988) J. Exp. Med. 167:1323; Kaiserlian D. et al. (1991) Eur. J. of Immunol. 21(10):2415; Look D. (1992) Am. J. of Physiol. 263(1):L79; Nonoyama S. et al. (1989) Eur. J. of Immunol. 19(9):1631; Singer K. et al. (1990) J. of Immunol. 144(8):2931), and its counter-receptor $\alpha^L\beta_2$ played a role in IEL-to-epithelial adhesion, it seems likely that IFN-γ acts to increase ICAM-1 expression on epithelial cells, thereby increasing the contribution of $\alpha^L\beta_2$ to IEL-to-epithelial cell adhesion. In addition, IFN-γ may influence the expression of an unidentified adhesion molecule which has a counter-receptor on IEL. In vivo, the net amount of IEL-to-epithelial cell adhesion is the result of the effects of many cytokines acting simultaneously on both cell types. The isolation of the effects of one cytokine on one of the cells is artificial and may not be relevant; however, as no effect on IEL-to-epithelial cell adhesion was seen if epithelial cell monolayers were pretreated with IL-1β, IL-4, or TNF-α the effect IFN-γ may be significant. Integrin utilization in the binding of IEL to epithelial cells is likely to be dependent on the local microenvironment.

As IEL are localized to the basolateral surface of epithelial cells in vivo, we proposed that the epithelial cell molecule recognized by $\alpha^E\beta_7$ might be localized to the basolateral surface of polarized epithelial cells. Several lines of evidence support this hypothesis. A significant percentage of IEL bound to the incompletely polarized 16E6.A5 cell line; however, they failed to adhere to the apical surface of confluent monolayers of the polarized cell line T84. When T84 cell tight junctions were disrupted allowing redistribution of basolaterally restricted molecules to the apical surface, IEL adhered well. IEL also adhered to subconfluent T84 cell monolayers, at the edges of cell clusters. In addition, coculture of trypsinized colonic epithelial cells with IEL resulted in a localization of IEL to basal and lateral locations in vitro, positions analogous that in vivo. Overall, these findings suggested to us that the epithelial cell ligands for $\alpha^E\beta_7$ and $\alpha^L\beta_2$ are localized to the basolateral surface of epithelial cells. We believe that $\alpha^E\beta_7$ is responsible for the specific anchoring of IEL to the basolateral surface of the epithelium in vivo via interaction with an epithelial cell ligand. The failure of an antibody specific for $\alpha^E\beta_7$ mAb to block the adhesion of IEL to activated endothelium suggests that the epithelial cell ligand for $\alpha^E\beta_7$ is distinct from known integrin receptors such as ICAM-1 and VCAM-1.

Example IV

Production and Chacterization of Anti-Epithelial Cell Monoclonal Antibodies which influence IEL Adhesion to Epithelial Cells The search for molecules mediating adhesive interactions between IEL and epithelial cells revealed a prominent role for two integrins, $\alpha^E\beta_7$ and $\alpha^L\beta_2$. While ICAM-1 is a known $\alpha^L\beta_2$ counter-receptor (which is expressed on the surface of epithelial cells including the 16E6.A5 cell line described above (Kaiserlian D. et al. (1991) Eur. J. of Immunol. 21(10):2415), no known ligand for $\alpha^E\beta_7$ has been reported. The static cell-to-cell adhesion system described in Example III indicated the likely presence of a cellular counter-receptor for $\alpha^E\beta_7$ on the surface of 16E6.A5 cells. In order to identify this cellular counter-receptor, anti-epithelial cell mAbs were generated and screened for their ability to alter IEL-to-epithelial cell adhesion.

Anti-epithelial cell mAb E4.6 blocks $\alpha^E\beta_7^+$ IEL but not $\alpha^E\beta_7^-$ PBL adhesion to 16E6.A5 epithelial cells Comparison of PBL to IEL in their capacity to bind the 16E6.A5 epithelial cell provided further correlation of the ability of the E4.6 mAb to block IEL-to-epithelial cell adhesion with the expression of $\alpha^E\beta_7$. While IEL grown in the presence of TGF-β1 express high levels of $\alpha^E\beta_7$ two weeks after stimulation with PHA, only a few percent of PBL express $\alpha^E\beta_7$ and only at very low levels. Both IEL and PBL bound the 16E6.A5 epithelial cell monolayer; however, the IEL adhered 34% better. IEL were blocked from binding the 16E6.A5 epithelial cell monolayer by 50–61% with three different mAbs which recognize the $\alpha^E\beta_7$ complex, and by 69% with the anti-epithelial cell mAb, E4.6. mAb recognizing other adhesion molecules expressed by IEL had little (21% for anti-β1 4B4) or no (TS 1/18 for $\alpha^L\beta_2$) effect on this adhesive interaction. In contrast, the adhesion of PBL to the 16E6.A5 epithelial cell was not inhibited by any of the mAbs tested. The inability of the E4.6 mAb to block the $\alpha^E\beta_7$ negative PBL adhesion to the 16E6.A5 epithelial cell monolayer suggested that the molecule recognized by the E4.6 mAb was a receptor for $\alpha^E\beta_7$.

The E4.6 mAb recognizes an antigen that is preferentially expressed in epithelial cells FACS analysis was performed on a panel of cell lines of different lineages to assess the distribution of expression of the E4.6 antigen. Expression was absent on the IEL line 032891, a B lymphoblastoid cell line (JY), a T cell tumor (Jurkat), monocytic cell lines (U937 and THP-1) and an NK-like cell line (YT) and low (MFI between 16 and 46) on three epithelial cell lines (HT29, A431 and 16E6.A5). Tissue staining of normal small intestine using indirect immunoperoxidase revealed that epithelial cells express the E4.6 antigen on their surface. The staining was specific to the basolateral membrane but not the apical surface. This type of restricted expression mirrors the location of IEL and is consistent with the expected distribution of an $\alpha^E\beta_7$ receptor. In addition, endothelial cells in the intestinal submucosa were stained with the E4.6 mAb. In tissue sections of tonsil, E4.6 staining was observed on the stratified squamous epithelial cells covering the luminal surface.

Biochemical characterization of mAbs E4.6 and E6.1 which inhibited IEL-to-epithelial cell adhesion Biochemical characterization of the antigen(s) recognized by the E4.6 and E6.1 mAbs was undertaken in order to determine their identity. 16E6.A5 cells were biosynthetically labeled, solubilized, and immunoprecipitated with control (P3), E4.6 or E6.1 mAbs. SDS-PAGE analysis under reduced conditions revealed that the pattern of radiolabeled species immunoprecipitated by E4.6 mAb was similar to that of E6.1 mAb. Prominent bands were seen at 126, 100 and 87 kDa. The 100 kDa band was broad and appeared to be an inadequately separated doublet. In addition, the E6.1 mAb also recognized a diffuse band ranging from 47–53 kDa. The difference in ability to precipitate antigen may be due to the fact that the E6.1 mAb is of the IgM isotype. As the E6.1 mAb was less efficient at precipitation and most likely recognized the same antigen as the E4.6 mAb, further biochemical characterization was carried out using the E4.6 mAb. To determine which of these bands represented the mature form of the protein present at the cell surface, 16E6.A5 cells were surface labeled by iodination, solubilized and immunoprecipitated with control (TCR-δ1) or E4.6 mAbs. SDS-PAGE analysis under nonreduced and DTT-reduced conditions showed a prominent band at 122 kDa which shifted to 124 kDa after reduction. Thus, only the largest biosynthetically labeled species was present at the cell surface.

The content of mature N-linked glycans on the surface labeled material was analyzed by digestion with N-glycanase. Following digestion under conditions which altered the size of class I molecules precipitated with the W6/32 mAb, the major band precipitated with E4.6 decreased in size from 117 kDa to a doublet of 107 and 100 kDa, suggesting that N-linked glycans were present. However, as the mature species may have been incompletely digested by the enzyme, the size of the peptide backbone was not determined. To continue the analysis, surface labeled, neuraminidase treated, material from the 16E6.A5 epithelial cell line was solubilized, immunoprecipitated with the E4.6 mAb, and allowed to migrate to its isoelectric point in the first dimension. In the second dimension, SDS-PAGE analysis under reducing conditions revealed two spots at approximately 120 kDa with acidic pIs of 5.1 and 4.8.

To understand the relationship of the surface protein with the other coprecipitated species visualized with biosynthetic labeling, pulse chase analysis was performed. 16E6.A5 cells were metabolically labeled for 15 min. with $^{35}S$ methionine and cysteine, chased with cold medium for different time points between 15 min. and 8 hrs, solubilized, immunoprecipitated with control (TCR-δ1) or E4.6 mAbs, and analyzed under reducing conditions by SDS-PAGE. After the 15 min. labeling period, 4 radiolabeled species were seen at 132, 102, 87 and 78 kDa. When allowed to mature for 15 min., a fifth band appeared at 123 kDa which had lower intensity. This pattern of 5 bands was seen again with 30 min. of chase time; however, by 1 hr., the 123 kDa band increased in intensity and by 4 hrs., the 123 kDa band was prominent while the 132 kDa band had disappeared. Finally, after 8 hrs. of chase time, four bands were visualized at 123, 102, 87 and 78 kDa. Knowing that the 123 kDa band is labeled at the cell surface, this pattern of bands is consistent with a precursor of the cell surface species being synthesized initially as a larger precursor molecule and associating immediately with three intracellular species. Then, between 15 min. and 4 hrs., being converted, possibly by cleavage, to the mature cell surface form at 123 kDa. The three intracellular bands at 102, 87 and 78 kDa were seen after the 15 min. labeling and remained invariant in SDS mobility as the cell surface form matured over 8 hrs.

Peptide mapping was performed to determine if the intracellular bands that associated with the precursor form were the same as those associated with the mature form. 16E6.A5 cells were biosynthetically labeled for 15 min. and chased for 0 or 4 hrs. before being solubilized, immunoprecipitated with the E4.6 mAb and separated by SDS-PAGE. The four bands visualized at each time point were cut out as a group to retain their size determined relationship to one another, rotated 90° and loaded on a second SDS-PAGE gel in the presence of V8 protease. At the 0 min. pulse-chase time point, the four bands were Ep (precursor), α, β, and γ, and at 240 min. they were Em (mature), α, β, and γ. After cleavage in the stacking gel, peptides were resolved by size. As the larger species were positioned on the left side of each group of four, comparison of the three peptide arrays (α, β, and γ) on the right showed the relationship of the intracellular bands at the two pulse-chase time points. Comparison of the peptides generated from each of the three invariant species (α, β, and γ) to the corresponding array seen with the other pulse-chase time point revealed an identical pattern. The array of peptides generated from the precursor and mature cell surface species revealed many shared but some unique bands. The presence of the extra piece in the precursor form (pulse-chase time 0 min.) resulted in the generation of peptides in each of the forms not shared by the other form.

Pulse chase analysis and peptide mapping revealed that the same three intracellular proteins (α, β, and γ) associated with both the precursor and mature form of the protein recognized by the E4.6 mAb. In an attempt to determine differences in the strength of association of the three bands coprecipitated with the E4.6 antigen, biosynthetically labeled material that was chased for 4 hrs., immunoprecipitated with E4.6, divided into several aliquots and eluted from the protein A sepharose beads with increasing pH for 20 min. at room temperature. At pH 8, the majority of the material remained on the beads; however, similar amounts of all four bands were eluted into the supernatant. When the pH was increased stepwise up to pH 11, more material was eluted from the beads but in each case all four bands were eluted with the same efficiency. This analysis suggests that all four proteins are strongly associated as no differential elution by pH was observed.

The antibodies which inhibit IEL-to-epithelial cell adhesion recognize E-cadherin Compiling the data presented above, the E4.6 antigen was expressed preferentially on the basolateral surface of epithelial cells as a 123 kDa protein which was originally synthesized as a 132 kDa precursor. The cell surface from contained N-linked glycans, had an acidic pI, and was associated with three intracellular proteins. These characteristics are hallmarks of the cadherin family of calcium-dependent cell adhesion molecules known to be important during morphogenesis (Takeichi M. (1991) Science 251:1451). Cadherins are associated with three cytoplasmic proteins, the catenins, which regulate their function (Nagafuchi A. et al. (1988) EMBO J. 7(12):3679; Ozawa M. et al. (1990) Proc. Natl. Acad. Sci. USA 87:4246). Catenins have been named α, β, and γ on the basis of their electrophoretic mobility (Kemler R. (1993) Trends in Gastroenterology 9:3 17). Based on size and tissue distribution, the most likely candidate for the E4.6 antigen was E-cadherin. To determine if the mAb which inhibited IEL-to-epithelial cell adhesion in that recognized the E-cadherin molecule, side by side immunoprecipitations were performed with mAb E4.6 and a known anti-cadherin mAb HECD-1. 16E6.A5 cells were biosynthetically labeled, solubilized, immunoprecipitated with background control (TCR-δ), E4.6, and HECD-1 mAbs (Shimoyama Y. et al. (1989) Cancer Research 49(8):2128), and analyzed by SDS-PAGE under reducing conditions. The pattern of radiolabeled species seen with the E4.6 mAb was identical to that seen with the HECD-1 mAb. The mature E-Cadherin band (Em) was seen at 126 kDa and four other bands were also present (α, β, γ and x). The three species at 123, 102, and 87 kDa are most likely α, β, and γ catenins based on size. The identity of the smallest species at 78 kDa is not known. However, since the smallest species was present in immunoprecipitations with both mAb E4.6 and mAb HECD-1 but not control mAb, it may be a precursor molecule or a previously unrecognized component of the E-cadherin complex. The species recognized by both the E4.6 and HECD-1 mAbs were confirmed as identical to one another with a two dimensional IEF/SDS-PAGE mixing experiment. 16E6.A5 cells were surface labeled with $^{125}$I, treated with neuraminidase, solubilized and immunoprecipitated with the E4.6 and HECD-1 mAbs. Three samples were run in the first dimension (IEF), the material immunoprecipitated with E4.6, HECD-1, and a mixture of the two. After the second dimension which separated proteins by size, the pattern of spots seen with E4.6, HECD-1, and E4.6+ HECD-1 were identical.

Discussion

In an attempt to identify an epithelial cell receptor for $\alpha^E\beta_7$, anti-epithelial cell mAbs were generated and screened for their ability to alter IEL-to-epithelial cell adhesion. The anti-epithelial cell mAbs produced which altered IEL-to-epithelial cell adhesion exhibited two different functional capabilities, those that enhanced and those that inhibited IEL-to-epithelial cell adhesion. Monoclonal antibodies that enhanced this interaction were determined to recognize CD44, a molecule with broad tissue distribution. These anti-CD44 mAb functioned to increase both IEL and PBL adhesion to epithelial cells. As PBL express at $\alpha^E\beta_7$ low levels, we concluded that the enhanced adhesion was not the result of an increase in $\alpha^E\beta_7$ mediated adhesion signaled by anti-CD44 mAb binding. As the anti-CD44 mAbs generated against the 16E6.A5 epithelial cell were able to block IEL binding to purified hyaluronic acid, it is unlikely that the increased adhesion was a direct result of an increase in the ability of CD44 to bind hyaluronic acid. It remains possible that these anti-CD44 mAb enhance the ability of CD44 to bind to an untested ligand(s) or that CD44 generates a signal in either the T cells or the epithelial cells which increases the ability of an adhesion molecule to bind its ligand on the other cell type. It is also possible that the bivalent CD44 mAbs bound one molecule of CD44 on each cell type resulting in cross-linking which increased the number of IEL bound to the epithelial cell by non-physiologic means.

Monoclonal antinbodies that inhibited IEL-to-epithelial cell adhesion were determined to recognize E-cadherin. Analysis of the expression and function of the anti-E-cadherin mAb indicated that E-cadherin is a candidate receptor for the $\alpha^E\beta_7$ integrin. It is expressed in a tissue restricted manner at the basolateral surface of epithelial cells, a distribution shared by IEL. Functionally, the E4.6 mAb could block T cell adhesion to epithelial cells only if the T cell expressed $\alpha^E\beta_7$. Thus, although E-cadherin is thought to be exclusively a homotypic adhesion molecule, it is not expressed by the cultured IEL line suggesting that it functions in this system as a heterotypic adhesion molecule mediating epithelial cell-to-IEL adhesion.

Example V

Role of E-Cadherin in $\alpha^E\beta_7$ Dependent Cell to Cell Adhesion

IEL-to-epithelial cell adhesion was inhibited by mAb which recognize $\alpha^E\beta_7$, a molecule expressed by IEL, and by mAb to E-cadherin, a molecule expressed by epithelial cells (Examples III and IV). As the ability of the anti-E-cadherin mAb to inhibit IEL-to-epithelial cell adhesion was dependent on the expression of $\alpha^E\beta_7$ by the IEL, we hypothesized that E-cadherin may be the counter-receptor for $\alpha^E\beta_7$. In an attempt to demonstrate that E-cadherin and $\alpha^E\beta_7$ interact, both molecules were transfected into cell lines lacking endogenous expression of either molecule and the resulting transfectants were analyzed for their ability to adhere to one another. Recipient cells transfected with either molecule, a control adhesion molecule, or vector alone were mixed in various combinations and their ability to bind to one another was determined. Further evidence defining the adhesion molecules being utilized in these transfected cell interactions was obtained through the use of monoclonal antibody blocking studies.

Transfection of E-cadherin

A full length human E-cadherin cDNA inserted into a eukaryotic expression vector containing the gene fiber resistance to the antibiotic G418 was obtained (David Rimm, Yale University). This E-cadherin construct was transfected into the murine fibroblast cell line, L-M. L-M cells do not express murine (Nagafuchi A. (1987) Nature 329:341) or human E-cadherin but do express the catenin proteins necessary for cadherin expression and function (Nagafuchi A. (1987) Nature 329:341; Ozawa M. et al. (1990) Proc. Natl. Acad. Sci. USA 87:4246). Stable transfectants were obtained by culturing L-M cells in the presence of G418. In the initial population, a small percentage of drug-resistant transfectants expressed E-cadherin. The positive cells were isolated by magnetic bead selection. After expansion, further selection for L-M cells expressing high levels of E-cadherin was carried out by sequential FACS sorting with the anti-E-cadherin mAb collecting the brightest 1% of stained L-M cells (see Materials and Methods). A cell line of transfectants was obtained which expressed E-cadherin with a MFI of 158 compared to a MF1 of 5 for L-M transfected with vector alone.

Adhesion of IEL to L-M transfectants

Cultured IEL cell lines expressing high levels of $\alpha^E\beta_7$ were analyzed for their ability to adhere to confluent monolayers of L-M cells transfected with either E-cadherin or vector alone. Comparison of the percent of IEL bound revealed that IEL adhered to E-cadherin transfectants 89% better than vector transfected L-M monolayers. In addition, the binding of IEL to E-cadherin transfectants was blocked by 48% with the anti-E-cadherin mAb E4.6 and 24–52% with mAb specific for $\alpha^E\beta_7$ (BerACT 8). Interestingly, the anti-E-cadherin mAb HECD-1, known to inhibit epithelial cell monolayer formation (Shimoyama Y. et al. (1989) Cancer Research 49(8):2128), had only a slight blocking effect on IEL adhesion to L-M E-cadherin transfectants in the representative experiment shown and no significant effect in other experiments. No blocking, but slight enhancement was seen with control mAbs which recognize integrin subunits $\beta 1$, $\beta 2$, or TCR-$\delta$. In contrast, the binding of IEL to vector transfected L-M was not inhibited by mAb which recognize either $\alpha^E\beta_7$ or E-cadherin; however, this interaction was blocked 48% by an anti-$\beta 1$ mAb. Thus, the ability of mAbs which recognize either $\alpha^E\beta_7$ or E-cadherin to inhibit IEL adhesion to L-M cells was dependent on the expression of both molecules, $\alpha^E\beta_7$ on the IEL and E-cadherin on the L-M cells.

Adhesion of PHA blasts to L-M transfectants

PBL were stimulated with PHA and grown in culture for two weeks before being tested for their ability to adhere to L-M monolayers transfected with E-cadherin or vector alone. Although binding of PHA blasts to both monolayers was low (14–19%), 36% more adhesion was observed to L-M vector transfected monolayers than E-cadherin transfected monolayers. No blocking was observed to either monolayer with mAb specific for E-cadherin, $\alpha^E\beta_7$, $\beta 1$, $\beta 2$, or TCR-$\delta$. The lack of expression of $\alpha^E\beta_7$ by the PHA blasts correlated with an absence of increased adhesion to the L-M monolayers expressing E-cadherin and a lack of inhibition of binding with mAb specific for either E-cadherin or $\alpha^E\beta_7$. Adhesion properties of COS-7 cells transfected with either $\alpha^E\beta_7$ or $\alpha^4\beta_7$ In order to isolate the function of $\alpha^E\beta_7$, COS-7 cells were transiently transfected with $\alpha^E\beta_7$ and used in binding assays to monolayers of various cells which were either positive or negative for E-cadherin expression. $\alpha^4\beta_7$ transfectants were also prepared and used as a control in these assays. The percent of COS-7 transfectants which expressed $\alpha^E\beta_7$ varied from experiment to experiment between 26% and 54%. Control transfections with $\alpha^4\beta_7$ were assessed with mAb to $\alpha^4$ which recognizes $\alpha^4$ when paired with either endogenous $\beta_1$ or transfected $\beta_7$ and the percent of cells expressing $\alpha^4$ varied between 49% and 58%. The percent of $\alpha^4$ paired with $\beta_1$ versus $\beta_7$ was not determined; however, the level of endogenous $\beta_1$ was similar on the $\alpha^E\beta_7$ (MFI, 268) and $\alpha^4\beta_7$ (MFI, 230) transfectants).

The $\alpha^E\beta_7$ and $\alpha^4\beta_7$ COS-7 transfectants were analyzed for their ability to adhere to confluent monolayers of 16E6.A5 mucosal epithelial cells. $\alpha^E\beta_7$ transfectants bound 267% better than $\alpha^4\beta_7$ transfectants to this E-cadherin expressing monolayer. Binding of the $\alpha^E\beta_7$ transfectants to the 16E6.A5 cells was blocked by the anti-E-cadherin specific mAb E4.6 (48%) and one anti-$\alpha^E\beta_7$ mAb (BerACT 8) (46–58%). Two additional anti-E-cadherin mAbs and mAbs to integrin subunits $\beta_1$ or $\beta_2$ did not inhibit this adhesion. The percent of $\alpha^4\beta_7$ COS-7 transfectants bound to the 16E6.A5 monolayer was low (9%) and none of the mAbs tested inhibited this adhesion.

The $\alpha^E\beta_7$ and $\alpha^4\beta_7$ COS-7 transfectants were also analyzed for their ability to adhere to confluent monolayers of L-M cells transfected with E-cadherin. $\alpha^E\beta_7$ transfectants bound 81% better than $\alpha^4\beta_7$ transfectants to this E-cadherin expressing monolayer. The binding of the $\alpha^E\beta_7$ transfectants to the L-M cells expressing E-cadherin was blocked by the E4.6 mAb specific for E-cadherin (45%) and three different mAbs which recognize $\alpha^E\beta_7$ (31%–41%). Two additional anti-E-cadherin mAbs and mAbs to $\beta_1$ or $\beta_2$ did not inhibit this adhesion. The percent of $\alpha^4\beta_7$ COS-7 transfectants bound to the monolayer of L-M cells expressing E-cadherin was low (16%). Adhesion of the $\alpha^4\beta_7$ transfectant was inhibited by the anti-$\beta_1$ mAb (25%) but not by any of the other mAbs tested.

In further experiments, the $\alpha^E\beta_7$ COS-7 transfectants were analyzed for their ability to adhere to confluent monolayers of L-M cells transfected with E-cadherin or to control L-M cells transfected with vector alone. $\alpha^E\beta_7$ transfectants bound 79% better to the L-M monolayers expressing E-cadherin than to vector alone transfected L-M monolayers. The binding of the $\alpha^E\beta_7$ transfectants to L-M cells expressing E-cadherin was blocked by the E4.6 mAb specific for E-cadherin (46%) and three different mAbs which recognize $\alpha^E\beta_7$ (46%–52%) to the level of adhesion observed with vector transfected L-M cells. mAbs to $\beta_1$ or $\beta_2$ did not inhibit this adhesion. $\alpha^E\beta_7$ transfectants bound to the monolayer of L-M cells expressing vector alone were not inhibited by any of the mAb tested.

Discussion

Study of the ability of mAbs specific for $\alpha^E\beta_7$ and E-cadherin to inhibit IEL-to-epithelial cell adhesion revealed that both of these molecules were important in the adhesion of IEL with epithelial cells. In an attempt to demonstrate that $\alpha^E\beta_7$ and E-cadherin directly interact, each was transfected into cells previously lacking expression of both molecules. The transfected cells were then allowed to interact with one another in various possible combinations. In these studies $\alpha^E\beta_7$ conferred adhesion only when E-cadherin was expressed on the adhering cell. The converse was also true. E-cadherin conferred adhesion only when $\alpha^E\beta_7$ was present on the adhering cell. The strength of interaction correlated with the expression of either molecule on the cell surface. In addition to the comparison of the amount of adhesion seen with each combination, mAb blocking studies were used to determine the specific molecules mediating the adhesion.

IEL bind to untransfected L-M fibroblast monolayers in an $\alpha^E\beta_7$ independent manner. However, transfection of E-cadherin into the L-M cells increased the percentage of IEL bound and this increased binding was blocked by mAb specific for either $\alpha^E\beta_7$ or the blocking anti-epithelial cell mAb characterized in Example IV to recognize E-cadherin. Thus, transfection of E-cadherin not only conferred E-cadherin but also $\alpha^E\beta_7$ dependent adhesion. In the other direction, transfection of into $\alpha^E\beta_7$ COS-7 cells conferred not only $\alpha^E\beta_7$ but also E-cadherin blockable binding to monolayers expressing E-cadherin.

The ability to transfect either $\alpha^E\beta_7$ or E-cadherin to a new cell type and confer specific adhesive function to that cell only when both molecules are present demonstrates that these two molecules are counter-receptors.

The specificity of the E-cadherin-to-$\alpha^E\beta_7$ adhesion was supported by the inability of $\alpha^4\beta_7$ transfectants to confer E-cadherin blockable binding. These results suggest that the $\alpha$ chain which pairs with $\beta_7$ is important in mediating E-cadherin dependent binding. However, as $\alpha^4$ can also pair with $\beta_1$ in the system studied, the lack of E-cadherin blockable binding may result from an insufficient level of expression of $\alpha^4\beta_7$. Analysis of the ability of a cell line which expresses high levels of $\alpha^4\beta_7$ and low levels of $\alpha^4\beta_1$ to adhere to E-cadherin transfectants is necessary to more rigorously determine the capacity of $\alpha^4\beta_7$ to bind to E-cadherin. In another system, the combination of one $\alpha$ chain ($\alpha^4$) with either of two $\beta$ chains ($\beta_1$ or $\beta_7$) has been shown to bind the same ligands (Chan B. M. C. et al. (1992) J. of Biol. Chem. 267:8366; Chan B. M. C. et al. (1992) Cell 68:1051; Ruegg C. et al. (1992) J. of Cell Biol. 117:179). Comparison of the ability of $\alpha^E\beta_7$ and or $\alpha^4\beta_7$ to bind to E-cadherin will determine if the combination of one $\beta$ chain ($\beta_7$) with either of two $\alpha$ chains ($\alpha^4$ or $\alpha^E$) can function to bind the same ligand.

The ability of four different E-cadherin antibodies to inhibit the proposed E-cadherin-to-$\alpha^E\beta_7$ adhesion was tested and only one was able to functionally inhibit the heterotypic cell-to-cell adhesion studied. Two of the mAbs, HECD-1 and DECMA-1, have been previously described to inhibit homotypic E-cadherin adhesion by disruption of epithelial cell monolayer formation (Shimoyama Y. et al. (1989) Cancer Research 49(8):2128; Vestweber D. et al. (1985) EMBO J. 4:3393). Their lack of inhibition of the proposed heterotypic E-cadherin-to-$\alpha^E\beta_7$ adhesion suggests that different domains of E-cadherin are important in these two independent adhesion events. In preliminary experiments, the anti-E-cadherin mAb E4.6, identified by its ability to inhibit IEL-to-epithelial cell adhesion, was unable to completely inhibit epithelial cell monolayer formation. In another system, two domains of ICAM-1 are used to bind different leukocyte integrins, the most N-terminal Ig domain binds $\alpha^L\beta_2$ while the third domain binds $\alpha^M\beta_2$ (Springer T. (1990) Nature 346(6283):425; Springer T. (1990) Annual Review of Cell Biol. 6:359). Thus, E-cadherin may utilize different domains to mediate homotypic versus heterotypic adhesive interactions.

Example VI

Identification of the Amino Acids Involved in E-cadherin binding to $\alpha^E\beta_7$.

Chimeric molecules of E- and P-cadherin in which analogous regions of each protein are exchanged are constructed to identify the regions of E-cadherin that are essential for binding with the $\alpha^E\beta_7$ integrin. (See, e.g., A. Nose, et al., Cell 61:147–155 (1990), for an exemplary procedure for preparing chimeric cadherin molecules. Restriction enzyme sites are introduced by in vitro mutagenesis at several positions in both molecules such that cDNA from each molecule can be interchanged. In particular, a restriction site is introduced into the cDNA at, or near, the nucleotide codon encoding amino acid 113, such that the 113 (of SEQ. ID. NOS. 1 or 2) N-terminal amino acid portion can be swapped. Other positions into which restriction sites are introduced are located at approximately 110 amino acid intervals. For example, in a first swap, amino acids 1–550 of E-cadherin (SEQ. ID. NOS. 1 or 2) are exchanged for the corresponding amino acid sequence in P-cadherin. In a second swap, amino acids 1–444 of E-cadherin (SEQ. ID. NOS. 1 or 2) are exchanged for the corresponding amino acid sequence in P-cadherin. In a like manner, amino acids 1–133, 1–123 and 1–113 of E-cadherin (SEQ. ID. NOS. 1 or 2) are sequentially exchanged for their respective, corresponding amino acid sequences in P-cadherin.

The chimeric cDNAs are transfected into LM cells by calcium phosphate precipitation. Chimeric cadherins are detected on the transfected cell surface using monoclonal antibodies to either E- or P-cadherin. Thereafter, the binding sites for the anti-E-cadherin mAbs E4.6 and E6.1, which inhibit $\alpha^E\beta_7$-mediated IEL-to-epithelial cell adhesion, are compared to the binding sites of HECD-1 and DECMA-1, which inhibit homotypic adhesion.

In the murine system, mAbs which inhibit homotypic adhesion map to amino acid numbers 78 and 83 (A. Nose, et al., Cell 61:147–155 (1990)). As mAbs which inhibit homotypic adhesion do not block the heterotypic adhesion of $\alpha^E\beta_7$ to E-cadherin, it it likely that E4.6 and E6.1 will map to a different amino acid location. To determine whether the chimeric cadherin proteins function in heterotypic adhesion, LM cells expressing each chimera that interacts with the EA.6 mAb is grown to confluence in 96 well plates and used as a substrate in an adhesion assay. IEL expressing high levels of $\alpha^E\beta_7$ are fluorescently labeled and are allowed to adhere to the LM monolayers for approximately 45 minutes. Unbound cells are removed by washing and the bound cells are enumerated. The specificity of the binding is assessed with mAb blocking. Here, the anti-E-cadherin mAb E4.6 is incubated with the chimeric proteins prior to the addition of the $\alpha^E\beta_7$-expressing IEL. Once a broad region of E-cadherin that is capable of conferring $\alpha^E\beta_7$-mediated adhesion is identified, smaller amino acid segment swaps within the identified region, as well as point mutations, are made to further define the binding site. In addition, other cadherins, including P-cadherin are assayed for their ability to support $\alpha^E\beta_7$-mediated adhesion. If P-cadherin is able to mediate adhesion, areas of similarity between the E- and P-cadherin are targeted as potential sites of interaction with $\alpha^E\beta_7$. In such an instance, a different cadherin which does not support $\alpha^E\beta_7$-mediated adhesion, e.g., N-cadherin, is substituted for P-cadherin in the above-described swapping experiment.

Example VII

An adhesion assay for selecting functionally equivalent peptide analogs

The adhesion assay described herein is based upon the assay described by Cepek, K., et al., in *J. Immunol*, 150(8):3459–3470 (1993), the entire contents of which are incorporated herein by reference.

The 16E6.A5 cell line was derived by immortalization of the 76N normal epithelial cell line through transfection of the E6 and E7 genes of human papilloma virus (by V. Band, Tufts University, publically available). Monolayers of these adherent cells are grown in flat-bottomed 96-well Linbro tissue culture plates. $10^4$ adherent cells in 100 ul complete media are added per well and allowed to grow for 3 days until they reach confluence. Just before the addition of iIEL, these cells are washed with assay media. To label iIEL, 25 µg of 2',7'-bis-(2-carboxyethyl)-5 (and 6)-carboxyfluorescein (BCEFC-AM, Molecular Probes, Inc., Eugene, Oreg.) is diluted in 5 µl DMSO and added to a suspension of $5\times10^6$/ml IEL in complete Yssel's media. The cells are incubated at 37° C. for 35 min then washed twice in assay media (phosphate buffered saline "PBS" or RPMI tissue culture media, available from GIBCO or Sigma Chemical Corp., St. Louis, Mo., containing 1 mM $CaCl_2$, 2 mM $MgCl_2$, and 10 mM HEPES). After washing, 50,000 labeled iIEL in 100 µl of assay media are added to the adherent cell monolayers. iIEL are allowed to settle onto adherent cell monolayers for 25 min or 40 min at 37° C. Unbound cells are removed by flicking media from the plate. Bound cells are detected using a Fluorescence plate reader (IDEXX Co., Portland Me.). If antibody blocking is performed, the iIEL are preincubated with an appropriate concentration of antibody (e.g., a 1/250 dilution of ascites fluid or 10 ug/ml of purified mAb) for 5 min at 37° C. before addition to the adherent cell monolayers. At least four replicates were performed. The % cells bound is calculated by reading the fluorescence units obtained after unbound cells are washed off and dividing this number by the input fluorescence units obtained after adding 50,000 cells/well and multiplying by 100. Serial dilutions of labeled cells have shown that as few as 1000 cells can be detected in the linear range.

To screen a molecular library or other mixture for the presence of a functionally equivalent peptide analog, the iIEL are washed with HBSS (Hanks buffered saline solution, available from Gibco) and pre-equilibrated with HBSS containing serial dilutions of the library or other peptide-containing solution (over a broad concentration range (e.g. 1 ng/ml to 100 ug/ml) for selected times (e.g., 30 min, 1 hour, 2 hours, 6 hours) at 37° C. before incubation with 16E6.A5 monolayers that have been washed with HBSS. Functionally equivalent peptide analogs are identified by their ability to inhibit the binding of cells to the monolayer of adherent cells.

It should be understood that the preceding is merely a detailed description of certain preferred embodiments. It therefore should be apparent to those skilled in the art that various modifications and equivalents can be made without departing from the spirit and scope of the invention.

A Sequence Listing is presented below and is followed by what is claimed.

We claim:

1. A composition comprising a monoclonal antibody that inhibits adhesion between a heterotypic cognate of E-cadherin expressed on a human T lymphocyte and a human E-cadherin expressing cell, wherein said monoclonal antibody specifically binds to the human E-cadherin and wherein the heterotypic cognate of E-cadherin is $\alpha^E\beta_7$.

2. The composition of claim 1, wherein the T lymphocyte is an intra-epithelial T lymphocyte.

3. The composition of claim 2, wherein the E-cadherin expressing cell is an epithelial cell or an endothelial cell.

4. The composition of claim 1, wherein the monoclonal antibody is monoclonal antibody E4.6 produced by ATCC designation HB 11996.

5. A pharmaceutical composition comprising:

an agent that inhibits adhesion in vivo between a T lymphocyte and a human E-cadherin expressing cell, wherein said agent is a monoclonal antibody that inhibits adhesion between a heterotypic cognate of E-cadherin expressed on a human T lymphocyte and a human E-cadherin expressing cell, and wherein said monoclonal antibody specifically binds to the human E-cadherin, and wherein the heterotypic cognate of E-cadherin is $\alpha^E\beta_7$; and a pharmaceutically acceptable carrier, wherein said monoclonal antibody is present in a therapeutically effective amount to treat a mucosal immune response.

6. The composition of claim 5, wherein the T lymphocyte is an intraepithelial T lymphocyte.

7. The composition of claim 5, wherein the E-cadherin expressing cell is selected from the group consisting of an epithelial cell and an endothelial cell.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2808 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapiens
        ( F ) TISSUE TYPE: liver ( i x ) FEATURE:
        ( A ) NAME/KEY: CDS
        ( B ) LOCATION: 109..2745

( i x ) FEATURE:
        ( A ) NAME/KEY: sig_peptide
        ( B ) LOCATION: 109..558

( i x ) FEATURE:
        ( A ) NAME/KEY: mat_peptide
        ( B ) LOCATION: 559..2742

( i x ) FEATURE:
        ( A ) NAME/KEY: cytoplasmic tail
        ( B ) LOCATION: 2296..2746

( i x ) FEATURE:
        ( A ) NAME/KEY: HAV tripeptide
        ( B ) LOCATION: 800..808

( i x ) FEATURE:
        ( A ) NAME/KEY: transmembrane
        ( B ) LOCATION: 2225..2295

( x i ) SEQUENCE DESCRIPTION: SEQ ID NO:1:

```
GGAAAGCACC TGTGAGCTTG GCAAGTCAGT TCAGAGCTCC AGCCCGCTCC AGCCCGGCCC          60

GACCCGACCG CACCCGGCGC CTGCCTCGCT CGGGCTCCCC GGCCAGCC ATG GGC CCT        117
                                                    Met Gly Pro
                                                    -150

TGG AGC CGC AGC CTC TCG GGC CTG CTG CTG CTG CTG AGG TCT CCT CTT         165
Trp Ser Arg Ser Leu Ser Gly Leu Leu Leu Leu Leu Arg Ser Pro Leu
       -145              -140                  -135

GGC TCT CAG GAG CGG AGC CCT CCT CCC TGT TTG ACG CGA GAG CTA CAC         213
Gly Ser Gln Glu Arg Ser Pro Pro Pro Cys Leu Thr Arg Glu Leu His
    -130                  -125                  -120

GTT CAC GGT GCC CCG GCG CCA CCT GAG AAG AGG CCG CGT CTG GGC AGA         261
Val His Gly Ala Pro Ala Pro Pro Glu Lys Arg Pro Arg Leu Gly Arg
-115                 -110                  -105                  -100

GTG AAT TTT GAA GAT TGC ACC GGT CGA CAA AGG ACA GCT ATT TTC CTG         309
Val Asn Phe Glu Asp Cys Thr Gly Arg Gln Arg Thr Ala Ile Phe Leu
                  -95                  -90                   -85

ACA CCG ATT CCG AAA GTG GGC ACA GAT GGT GTG ATT ACA GTC AAA AGG         357
Thr Pro Ile Pro Lys Val Gly Thr Asp Gly Val Ile Thr Val Lys Arg
                -80                   -75                   -70

CCT CTA CGG TTT CAT AAC CCA ACA GAT CCA TTT CTT GGT CTA CGC TGG         405
Pro Leu Arg Phe His Asn Pro Thr Asp Pro Phe Leu Gly Leu Arg Trp
```

|  |  |  |  |  |  |  |  |  |  |  |  |  |  |  |  |
|---|---|---|---|---|---|---|---|---|---|---|---|---|---|---|---|
|  | -65 |  |  |  |  | -60 |  |  |  |  | -55 |  |  |  |  |
| GAC | TCC | ACC | TAC | AGA | AAG | TTT | TCC | ACC | AAA | GTC | ACG | CTG | AAT | ACA | GTG | 453
| Asp | Ser | Thr | Tyr | Arg | Lys | Phe | Ser | Thr | Lys | Val | Thr | Leu | Asn | Thr | Val |
|  | -50 |  |  |  |  | -45 |  |  |  |  | -40 |  |  |  |  |
| GGG | CAC | CAC | CAC | CGC | CCC | CCG | CCC | CAT | CAG | GCC | TCC | GTT | TCT | GGA | ATC | 501
| Gly | His | His | His | Arg | Pro | Pro | Pro | His | Gln | Ala | Ser | Val | Ser | Gly | Ile |
| -35 |  |  |  |  | -30 |  |  |  |  | -25 |  |  |  |  | -20 |
| CAA | GCA | GAA | TTG | CTC | ACA | TTT | CCC | AAC | TCC | TCT | CCT | GGC | CTC | AGA | AGA | 549
| Gln | Ala | Glu | Leu | Leu | Thr | Phe | Pro | Asn | Ser | Ser | Pro | Gly | Leu | Arg | Arg |
|  |  |  |  | -15 |  |  |  |  | -10 |  |  |  |  | -5 |  |
| CAG | AAG | AGA | GAC | TGG | GTT | ATT | CCT | CCC | ATC | AGC | TGC | CCA | GAA | AAT | GAA | 597
| Gln | Lys | Arg | Asp | Trp | Val | Ile | Pro | Pro | Ile | Ser | Cys | Pro | Glu | Asn | Glu |
|  |  |  |  | 1 |  |  |  |  | 5 |  |  |  |  | 10 |  |
| AAA | GGC | CCA | TTT | CCT | AAA | AAC | CTG | GTT | CAG | ATC | AAA | TCC | AAC | AAA | GAC | 645
| Lys | Gly | Pro | Phe | Pro | Lys | Asn | Leu | Val | Gln | Ile | Lys | Ser | Asn | Lys | Asp |
|  | 15 |  |  |  |  | 20 |  |  |  |  | 25 |  |  |  |  |
| AAA | GAA | GGC | AAG | GTT | TTC | TAC | AGC | ATC | ACT | GGC | CAA | GGA | GCT | GAC | ACA | 693
| Lys | Glu | Gly | Lys | Val | Phe | Tyr | Ser | Ile | Thr | Gly | Gln | Gly | Ala | Asp | Thr |
| 30 |  |  |  |  | 35 |  |  |  |  | 40 |  |  |  |  | 45 |
| CCC | CCT | GTT | GGT | GTC | TTT | ATT | ATT | GAA | AGA | GAA | ACA | GGA | TGG | CTG | AAG | 741
| Pro | Pro | Val | Gly | Val | Phe | Ile | Ile | Glu | Arg | Glu | Thr | Gly | Trp | Leu | Lys |
|  |  |  |  | 50 |  |  |  |  | 55 |  |  |  |  | 60 |  |
| GTG | ACA | GAG | CCT | CTG | GAT | AGA | GAA | CGC | ATT | GCC | ACA | TAC | ACT | CTC | TTC | 789
| Val | Thr | Glu | Pro | Leu | Asp | Arg | Glu | Arg | Ile | Ala | Thr | Tyr | Thr | Leu | Phe |
|  |  |  | 65 |  |  |  |  | 70 |  |  |  |  | 75 |  |  |
| TCT | CAC | GCT | GTG | TCA | TCC | AAC | GGG | AAT | GCA | GTT | GAG | GAT | CCA | ATG | GAG | 837
| Ser | His | Ala | Val | Ser | Ser | Asn | Gly | Asn | Ala | Val | Glu | Asp | Pro | Met | Glu |
|  |  | 80 |  |  |  |  | 85 |  |  |  |  | 90 |  |  |  |
| ATT | TTG | ATC | ACG | GTA | ACC | GAT | CAG | AAT | GAC | AAC | AAG | CCC | GAA | TTC | ACC | 885
| Ile | Leu | Ile | Thr | Val | Thr | Asp | Gln | Asn | Asp | Asn | Lys | Pro | Glu | Phe | Thr |
|  |  | 95 |  |  |  |  | 100 |  |  |  |  | 105 |  |  |  |
| CAG | GAG | GTC | TTT | AAG | GGG | TCT | GTC | ATG | GAA | GGT | GCT | CTT | CCA | GGA | ACC | 933
| Gln | Glu | Val | Phe | Lys | Gly | Ser | Val | Met | Glu | Gly | Ala | Leu | Pro | Gly | Thr |
| 110 |  |  |  |  | 115 |  |  |  |  | 120 |  |  |  |  | 125 |
| TCT | GTG | ATG | GAG | GTC | ACA | GCC | ACA | GAC | GCG | GAC | GAT | GAT | GTG | AAC | ACC | 981
| Ser | Val | Met | Glu | Val | Thr | Ala | Thr | Asp | Ala | Asp | Asp | Asp | Val | Asn | Thr |
|  |  |  |  | 130 |  |  |  |  | 135 |  |  |  |  | 140 |  |
| TAC | AAT | GCC | GCC | ATC | GCT | TAC | ACC | ATC | CTC | AGC | CAA | GAT | CCT | GAG | CTC | 1029
| Tyr | Asn | Ala | Ala | Ile | Ala | Tyr | Thr | Ile | Leu | Ser | Gln | Asp | Pro | Glu | Leu |
|  |  |  | 145 |  |  |  |  | 150 |  |  |  |  | 155 |  |  |
| CCT | GAC | AAA | AAT | ATG | TTC | ACC | ATT | AAC | AGG | AAC | ACA | GGA | GTC | ATC | AGT | 1077
| Pro | Asp | Lys | Asn | Met | Phe | Thr | Ile | Asn | Arg | Asn | Thr | Gly | Val | Ile | Ser |
|  |  | 160 |  |  |  |  | 165 |  |  |  |  | 170 |  |  |  |
| GTG | GTC | ACC | ACT | GGG | CTG | GAC | CGA | GAG | AGT | TTC | CCT | ACG | TAT | ACC | CTG | 1125
| Val | Val | Thr | Thr | Gly | Leu | Asp | Arg | Glu | Ser | Phe | Pro | Thr | Tyr | Thr | Leu |
|  | 175 |  |  |  |  | 180 |  |  |  |  | 185 |  |  |  |  |
| GTG | GTT | CAA | GCT | GCT | GAC | CTT | CAA | GGT | GAG | GGG | TTA | AGC | ACA | ACA | GCA | 1173
| Val | Val | Gln | Ala | Ala | Asp | Leu | Gln | Gly | Glu | Gly | Leu | Ser | Thr | Thr | Ala |
| 190 |  |  |  |  | 195 |  |  |  |  | 200 |  |  |  |  | 205 |
| ACA | GCT | GTG | ATC | ACA | GTC | ACT | GAC | ACC | AAC | GAT | AAT | CCT | CCG | ATC | TTC | 1221
| Thr | Ala | Val | Ile | Thr | Val | Thr | Asp | Thr | Asn | Asp | Asn | Pro | Pro | Ile | Phe |
|  |  |  |  | 210 |  |  |  |  | 215 |  |  |  |  | 220 |  |
| AAT | CCC | ACC | ACG | TAC | AAG | GGT | CAG | GTG | CCT | GAG | AAC | GAG | GCT | AAC | GTC | 1269
| Asn | Pro | Thr | Thr | Tyr | Lys | Gly | Gln | Val | Pro | Glu | Asn | Glu | Ala | Asn | Val |
|  |  |  |  | 225 |  |  |  |  | 230 |  |  |  |  | 235 |  |
| GTA | ATC | ACC | ACA | CTG | AAA | GTG | ACT | GAT | GCT | GAT | GCC | CCC | AAT | ACC | CCA | 1317
| Val | Ile | Thr | Thr | Leu | Lys | Val | Thr | Asp | Ala | Asp | Ala | Pro | Asn | Thr | Pro |
|  |  | 240 |  |  |  |  | 245 |  |  |  |  | 250 |  |  |  |
| GCG | TGG | GAG | GCT | GTA | TAC | ACC | ATA | TTG | AAT | GAT | GAT | GGT | GGA | CAA | TTT | 1365
| Ala | Trp | Glu | Ala | Val | Tyr | Thr | Ile | Leu | Asn | Asp | Asp | Gly | Gly | Gln | Phe |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 255 |     |     |     | 260 |     |     |     |     | 265 |     |     |     |     |      |
| GTC | GTC | ACC | ACA | AAT | CCA | GTG | AAC | AAC | GAT | GGC | ATT | TTG | AAA | ACA | GCA | 1413 |
| Val | Val | Thr | Thr | Asn | Pro | Val | Asn | Asn | Asp | Gly | Ile | Leu | Lys | Thr | Ala |      |
| 270 |     |     |     | 275 |     |     |     |     | 280 |     |     |     |     | 285 |     |      |
| AAG | GGC | TTG | GAT | TTT | GAG | GCC | AAG | CAG | CAG | TAC | ATT | CTA | CAC | GTA | GCA | 1461 |
| Lys | Gly | Leu | Asp | Phe | Glu | Ala | Lys | Gln | Gln | Tyr | Ile | Leu | His | Val | Ala |      |
|     |     |     |     | 290 |     |     |     | 295 |     |     |     |     | 300 |     |     |      |
| GTG | ACG | AAT | GTG | GTA | CCT | TTT | GAG | GTC | TCT | CTC | ACC | ACC | TCC | ACA | GCC | 1509 |
| Val | Thr | Asn | Val | Val | Pro | Phe | Glu | Val | Ser | Leu | Thr | Thr | Ser | Thr | Ala |      |
|     |     |     | 305 |     |     |     |     | 310 |     |     |     |     | 315 |     |     |      |
| ACC | GTC | ACC | GTG | GAT | GTG | CTG | GAT | GTG | AAT | GAA | GGC | CCC | ATC | TTT | GTG | 1557 |
| Thr | Val | Thr | Val | Asp | Val | Leu | Asp | Val | Asn | Glu | Gly | Pro | Ile | Phe | Val |      |
|     |     | 320 |     |     |     |     | 325 |     |     |     |     | 330 |     |     |     |      |
| CCT | CCT | GAA | AAG | AGA | GTG | GAA | GTG | TCC | GAG | GAC | TTT | GGC | GTG | GGC | CAG | 1605 |
| Pro | Pro | Glu | Lys | Arg | Val | Glu | Val | Ser | Glu | Asp | Phe | Gly | Val | Gly | Gln |      |
|     | 335 |     |     |     |     | 340 |     |     |     |     | 345 |     |     |     |     |      |
| GAA | ATC | ACA | TCC | TAC | ACT | GCC | CAG | GAG | CCA | GAC | ACA | TTT | ATG | GAA | CAG | 1653 |
| Glu | Ile | Thr | Ser | Tyr | Thr | Ala | Gln | Glu | Pro | Asp | Thr | Phe | Met | Glu | Gln |      |
| 350 |     |     |     |     | 355 |     |     |     |     | 360 |     |     |     |     | 365 |      |
| AAA | ATA | ACA | TAT | CGG | ATT | TGG | AGA | GAC | ACT | CGC | AAC | TGG | CTG | GAG | ATT | 1701 |
| Lys | Ile | Thr | Tyr | Arg | Ile | Trp | Arg | Asp | Thr | Arg | Asn | Trp | Leu | Glu | Ile |      |
|     |     |     |     | 370 |     |     |     | 375 |     |     |     |     | 380 |     |     |      |
| AAT | CCG | GAC | ACT | GGT | GCC | ATT | TCC | ACT | CGG | GCT | GAG | CTG | GAC | AGG | GAG | 1749 |
| Asn | Pro | Asp | Thr | Gly | Ala | Ile | Ser | Thr | Arg | Ala | Glu | Leu | Asp | Arg | Glu |      |
|     |     || 385 |     |     |     | 390 |     |     |     |     | 395 |     |     |      |
| GAT | TTT | GAG | CAC | GTG | AAG | AAC | AGC | ACG | TAC | ACA | GCC | CTA | ATC | ATA | GCT | 1797 |
| Asp | Phe | Glu | His | Val | Lys | Asn | Ser | Thr | Tyr | Thr | Ala | Leu | Ile | Ile | Ala |      |
|     |     | 400 |     |     |     |     | 405 |     |     |     |     | 410 |     |     |     |      |
| ACA | GAC | AAT | GGT | TCT | CCA | GTT | GCT | ACT | GGA | ACA | GGG | ACA | CTT | CTG | CTG | 1845 |
| Thr | Asp | Asn | Gly | Ser | Pro | Val | Ala | Thr | Gly | Thr | Gly | Thr | Leu | Leu | Leu |      |
|     | 415 |     |     |     |     | 420 |     |     |     |     | 425 |     |     |     |     |      |
| ATC | CTG | TCT | GAT | GTG | AAT | GAC | AAC | GCC | CCC | ATA | CCA | GAA | CCT | CGA | ACT | 1893 |
| Ile | Leu | Ser | Asp | Val | Asn | Asp | Asn | Ala | Pro | Ile | Pro | Glu | Pro | Arg | Thr |      |
| 430 |     |     |     |     | 435 |     |     |     |     | 440 |     |     |     |     | 445 |      |
| ATA | TTC | TTC | TGT | GAG | AGG | AAT | CCA | AAG | CCT | CAG | GTC | ATA | AAC | ATT | CAT | 1941 |
| Ile | Phe | Phe | Cys | Glu | Arg | Asn | Pro | Lys | Pro | Gln | Val | Ile | Asn | Ile | His |      |
|     |     |     |     | 450 |     |     |     | 455 |     |     |     |     | 460 |     |     |      |
| GAT | GCA | GAC | CTT | CCT | CCC | AAT | ACA | TCT | CCC | TTC | ACA | GCA | GAA | CTA | ACA | 1989 |
| Asp | Ala | Asp | Leu | Pro | Pro | Asn | Thr | Ser | Pro | Phe | Thr | Ala | Glu | Leu | Thr |      |
|     |     |     | 465 |     |     |     |     | 470 |     |     |     |     | 475 |     |     |      |
| CAC | GGG | CGA | GTG | CCC | AAC | TGG | ACC | ATT | CAG | TAC | AAC | GAC | CCA | ACC | CAA | 2037 |
| His | Gly | Arg | Val | Pro | Asn | Trp | Thr | Ile | Gln | Tyr | Asn | Asp | Pro | Thr | Gln |      |
|     |     | 480 |     |     |     |     | 485 |     |     |     |     | 490 |     |     |     |      |
| GAA | TCT | ATC | ATT | TTG | AAG | CCA | AAG | ATG | GCC | TTA | GAG | GTG | GGT | GAC | TAC | 2085 |
| Glu | Ser | Ile | Ile | Leu | Lys | Pro | Lys | Met | Ala | Leu | Glu | Val | Gly | Asp | Tyr |      |
|     | 495 |     |     |     |     | 500 |     |     |     |     | 505 |     |     |     |     |      |
| AAA | ATC | AAT | CTC | AAG | CTC | ATG | GAT | AAC | CAG | AAT | AAA | GAC | CAA | GTG | ACC | 2133 |
| Lys | Ile | Asn | Leu | Lys | Leu | Met | Asp | Asn | Gln | Asn | Lys | Asp | Gln | Val | Thr |      |
| 510 |     |     |     |     | 515 |     |     |     |     | 520 |     |     |     |     | 525 |      |
| ACC | TTA | GAG | GTC | AGC | GTG | TGT | GAC | TGT | GAA | GGG | GCC | GCC | GGC | GTC | TGT | 2181 |
| Thr | Leu | Glu | Val | Ser | Val | Cys | Asp | Cys | Glu | Gly | Ala | Ala | Gly | Val | Cys |      |
|     |     |     |     | 530 |     |     |     |     | 535 |     |     |     |     | 540 |     |      |
| AGG | AAG | GCA | CAG | CCT | GTC | GAA | GCA | GGA | TTG | CAA | ATT | CCT | GCC | ATT | CTG | 2229 |
| Arg | Lys | Ala | Gln | Pro | Val | Glu | Ala | Gly | Leu | Gln | Ile | Pro | Ala | Ile | Leu |      |
|     |     |     | 545 |     |     |     |     | 550 |     |     |     |     | 555 |     |     |      |
| GGG | ATT | CTT | GGA | GGA | ATT | CTT | GCT | TTG | CTA | ATT | CTG | ATT | CTG | CTG | CTC | 2277 |
| Gly | Ile | Leu | Gly | Gly | Ile | Leu | Ala | Leu | Leu | Ile | Leu | Ile | Leu | Leu | Leu |      |
|     |     | 560 |     |     |     |     | 565 |     |     |     |     | 570 |     |     |     |      |
| TTG | CTG | TTT | CTT | CGG | AGG | AGA | GCG | GTG | GTC | AAA | GAG | CCC | TTA | CTG | CCC | 2325 |
| Leu | Leu | Phe | Leu | Arg | Arg | Arg | Ala | Val | Val | Lys | Glu | Pro | Leu | Leu | Pro |      |

|     |     |     | 575 |     |     |     |     | 580 |     |     |     |     | 585 |     |     |      |
|-----|-----|-----|-----|-----|-----|-----|-----|-----|-----|-----|-----|-----|-----|-----|-----|------|
| CCA | GAG | GAT | GAC | ACC | CGG | GAC | AAC | GTT | TAT | TAC | TAT | GAT | GAA | GAA | GGA | 2373 |
| Pro | Glu | Asp | Asp | Thr | Arg | Asp | Asn | Val | Tyr | Tyr | Tyr | Asp | Glu | Glu | Gly |      |
| 590 |     |     |     |     | 595 |     |     |     | 600 |     |     |     |     |     | 605 |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| GGC | GGA | GAA | GAG | GAC | CAG | GAC | TTT | GAC | TTG | AGC | CAG | CTG | CAC | AGG | GGC | 2421 |
| Gly | Gly | Glu | Glu | Asp | Gln | Asp | Phe | Asp | Leu | Ser | Gln | Leu | His | Arg | Gly |      |
|     |     |     |     | 610 |     |     |     |     | 615 |     |     |     |     | 620 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| CTG | GAC | GCT | CGG | CCT | GAA | GTG | ACT | CGT | AAC | GAC | GTT | GCA | CCA | ACC | CTC | 2469 |
| Leu | Asp | Ala | Arg | Pro | Glu | Val | Thr | Arg | Asn | Asp | Val | Ala | Pro | Thr | Leu |      |
|     |     |     | 625 |     |     |     |     | 630 |     |     |     |     | 635 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ATG | AGT | GTC | CCC | CGG | TAT | CTT | CCC | CGC | CCT | GCC | AAT | CCC | GAT | GAA | ATT | 2517 |
| Met | Ser | Val | Pro | Arg | Tyr | Leu | Pro | Arg | Pro | Ala | Asn | Pro | Asp | Glu | Ile |      |
|     |     |     | 640 |     |     |     | 645 |     |     |     |     | 650 |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| GGA | AAT | TTT | ATT | GAT | GAA | AAT | CTG | AAA | GCG | GCT | GAT | ACT | GAC | CCC | ACA | 2565 |
| Gly | Asn | Phe | Ile | Asp | Glu | Asn | Leu | Lys | Ala | Ala | Asp | Thr | Asp | Pro | Thr |      |
|     |     | 655 |     |     |     | 660 |     |     |     |     | 665 |     |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| GCC | CCG | CCT | TAT | GAT | TCT | CTG | CTC | GTG | TTT | GAC | TAT | GAA | GGA | AGC | GGT | 2613 |
| Ala | Pro | Pro | Tyr | Asp | Ser | Leu | Leu | Val | Phe | Asp | Tyr | Glu | Gly | Ser | Gly |      |
| 670 |     |     |     |     | 675 |     |     |     |     | 680 |     |     |     |     | 685 |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| TCC | GAA | GCT | GCT | AGT | CTG | AGC | TCC | CTG | AAC | TCC | TCA | GAG | TCA | GAC | AAA | 2661 |
| Ser | Glu | Ala | Ala | Ser | Leu | Ser | Ser | Leu | Asn | Ser | Ser | Glu | Ser | Asp | Lys |      |
|     |     |     |     | 690 |     |     |     |     | 695 |     |     |     |     | 700 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| GAC | CAG | GAC | TAT | GAC | TAC | TTG | AAC | GAA | TGG | GGC | AAT | CGC | TTC | AAG | AAG | 2709 |
| Asp | Gln | Asp | Tyr | Asp | Tyr | Leu | Asn | Glu | Trp | Gly | Asn | Arg | Phe | Lys | Lys |      |
|     |     |     | 705 |     |     |     |     | 710 |     |     |     |     | 715 |     |     |      |

|     |     |     |     |     |     |     |     |     |     |            |            |      |
|-----|-----|-----|-----|-----|-----|-----|-----|-----|-----|------------|------------|------|
| CTG | GCT | GAC | ATG | TAC | GGA | GGC | GGC | GAG | GAC | CAC        | TAGGGACTC  | GAGAGAGGCG | 2762 |
| Leu | Ala | Asp | Met | Tyr | Gly | Gly | Gly | Glu | Asp | His        |            |      |
|     |     | 720 |     |     |     | 725 |     |     |     |            |            |      |

GCCCAGACCA TGTGCAGAAA TGCAGAAATC AGCGTTCTGG TGTTTT                                2808

( 2 ) INFORMATION FOR SEQ ID NO:2:

( i ) SEQUENCE CHARACTERISTICS:
        ( A ) LENGTH: 878 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met  | Gly | Pro | Trp | Ser  | Arg | Ser | Leu | Ser  | Gly | Leu | Leu | Leu  | Leu | Leu | Arg  |
|------|-----|-----|-----|------|-----|-----|-----|------|-----|-----|-----|------|-----|-----|------|
| -150 |     |     |     | -145 |     |     |     | -140 |     |     |     | -135 |     |     |      |

| Ser | Pro | Leu | Gly  | Ser | Gln | Glu | Arg | Ser  | Pro | Pro | Pro | Cys  | Leu | Thr | Arg  |
|-----|-----|-----|------|-----|-----|-----|-----|------|-----|-----|-----|------|-----|-----|------|
|     |     |     | -130 |     |     |     |     | -125 |     |     |     | -120 |     |     |      |

| Glu | Leu | His | Val  | His | Gly | Ala | Pro | Ala  | Pro | Pro | Glu | Lys | Arg  | Pro | Arg |
|-----|-----|-----|------|-----|-----|-----|-----|------|-----|-----|-----|-----|------|-----|-----|
|     |     |     | -115 |     |     |     |     | -110 |     |     |     |     | -105 |     |     |

| Leu | Gly | Arg | Val  | Asn | Phe | Glu | Asp | Cys  | Thr | Gly | Arg | Gln | Arg  | Thr | Ala |
|-----|-----|-----|------|-----|-----|-----|-----|------|-----|-----|-----|-----|------|-----|-----|
|     |     |     | -100 |     |     |     |     | -95  |     |     |     |     | -90  |     |     |

| Ile | Phe | Leu | Thr | Pro | Ile | Pro | Lys | Val | Gly | Thr | Asp | Gly | Val | Ile | Thr |
|-----|-----|-----|-----|-----|-----|-----|-----|-----|-----|-----|-----|-----|-----|-----|-----|
|     | -85 |     |     |     | -80 |     |     |     |     |     | -75 |     |     |     |     |

| Val | Lys | Arg | Pro | Leu | Arg | Phe | His | Asn | Pro | Thr | Asp | Pro | Phe | Leu | Gly |
|-----|-----|-----|-----|-----|-----|-----|-----|-----|-----|-----|-----|-----|-----|-----|-----|
| -70 |     |     |     |     | -65 |     |     |     |     |     | -60 |     |     |     | -55 |

| Leu | Arg | Trp | Asp | Ser | Thr | Tyr | Arg | Lys | Phe | Ser | Thr | Lys | Val | Thr | Leu |
|-----|-----|-----|-----|-----|-----|-----|-----|-----|-----|-----|-----|-----|-----|-----|-----|
|     |     |     |     | -50 |     |     |     |     | -45 |     |     |     |     |     | -40 |

| Asn | Thr | Val | Gly | His | His | His | Arg | Pro | Pro | His | Gln | Ala | Ser | Val |
|-----|-----|-----|-----|-----|-----|-----|-----|-----|-----|-----|-----|-----|-----|-----|
|     |     |     | -35 |     |     |     |     | -30 |     |     |     | -25 |     |     |

| Ser | Gly | Ile | Gln  | Ala | Glu | Leu | Leu  | Thr | Phe | Pro | Asn  | Ser | Ser | Pro | Gly |
|-----|-----|-----|------|-----|-----|-----|------|-----|-----|-----|------|-----|-----|-----|-----|
|     |     |     | -20  |     |     |     | -15  |     |     |     | -10  |     |     |     |     |

| Leu | Arg | Arg | Gln | Lys | Arg | Asp | Trp | Val | Ile | Pro | Pro | Ile | Ser | Cys | Pro |

```
      - 5                    1                   5                        10
 Glu  Asn  Glu  Lys  Gly  Pro  Phe  Pro  Lys  Asn  Leu  Val  Gln  Ile  Lys  Ser
                15                   20                        25
 Asn  Lys  Asp  Lys  Glu  Gly  Lys  Val  Phe  Tyr  Ser  Ile  Thr  Gly  Gln  Gly
                30                        35                   40
 Ala  Asp  Thr  Pro  Pro  Val  Gly  Val  Phe  Ile  Ile  Glu  Arg  Glu  Thr  Gly
                45                        50                   55
 Trp  Leu  Lys  Val  Thr  Glu  Pro  Leu  Asp  Arg  Glu  Arg  Ile  Ala  Thr  Tyr
           60                   65                   70
 Thr  Leu  Phe  Ser  His  Ala  Val  Ser  Ser  Asn  Gly  Asn  Ala  Val  Glu  Asp
      75                   80                   85                        90
 Pro  Met  Glu  Ile  Leu  Ile  Thr  Val  Thr  Asp  Gln  Asn  Asp  Asn  Lys  Pro
                     95                        100                 105
 Glu  Phe  Thr  Gln  Glu  Val  Phe  Lys  Gly  Ser  Val  Met  Glu  Gly  Ala  Leu
                     110                       115                 120
 Pro  Gly  Thr  Ser  Val  Met  Glu  Val  Thr  Ala  Thr  Asp  Ala  Asp  Asp  Asp
                125                       130                 135
 Val  Asn  Thr  Tyr  Asn  Ala  Ala  Ile  Ala  Tyr  Thr  Ile  Leu  Ser  Gln  Asp
      140                       145                 150
 Pro  Glu  Leu  Pro  Asp  Lys  Asn  Met  Phe  Thr  Ile  Asn  Arg  Asn  Thr  Gly
 155                 160                       165                      170
 Val  Ile  Ser  Val  Val  Thr  Thr  Gly  Leu  Asp  Arg  Glu  Ser  Phe  Pro  Thr
                     175                       180                 185
 Tyr  Thr  Leu  Val  Val  Gln  Ala  Ala  Asp  Leu  Gln  Gly  Glu  Gly  Leu  Ser
                     190                       195                 200
 Thr  Thr  Ala  Thr  Ala  Val  Ile  Thr  Val  Thr  Asp  Thr  Asn  Asp  Asn  Pro
                205                       210                 215
 Pro  Ile  Phe  Asn  Pro  Thr  Thr  Tyr  Lys  Gly  Gln  Val  Pro  Glu  Asn  Glu
 220                       225                 230
 Ala  Asn  Val  Val  Ile  Thr  Thr  Leu  Lys  Val  Thr  Asp  Ala  Asp  Ala  Pro
 235                 240                       245                      250
 Asn  Thr  Pro  Ala  Trp  Glu  Ala  Val  Tyr  Thr  Ile  Leu  Asn  Asp  Asp  Gly
                255                       260                      265
 Gly  Gln  Phe  Val  Val  Thr  Thr  Asn  Pro  Val  Asn  Asn  Asp  Gly  Ile  Leu
                     270                       275                 280
 Lys  Thr  Ala  Lys  Gly  Leu  Asp  Phe  Glu  Ala  Lys  Gln  Gln  Tyr  Ile  Leu
                285                       290                 295
 His  Val  Ala  Val  Thr  Asn  Val  Val  Pro  Phe  Glu  Val  Ser  Leu  Thr  Thr
      300                       305                 310
 Ser  Thr  Ala  Thr  Val  Thr  Val  Asp  Val  Leu  Asp  Val  Asn  Glu  Gly  Pro
 315                       320                 325                      330
 Ile  Phe  Val  Pro  Pro  Glu  Lys  Arg  Val  Glu  Val  Ser  Glu  Asp  Phe  Gly
                335                       340                 345
 Val  Gly  Gln  Glu  Ile  Thr  Ser  Tyr  Thr  Ala  Gln  Glu  Pro  Asp  Thr  Phe
                350                       355                 360
 Met  Glu  Gln  Lys  Ile  Thr  Tyr  Arg  Ile  Trp  Arg  Asp  Thr  Arg  Asn  Trp
                365                       370                 375
 Leu  Glu  Ile  Asn  Pro  Asp  Thr  Gly  Ala  Ile  Ser  Thr  Arg  Ala  Glu  Leu
      380                       385                 390
 Asp  Arg  Glu  Asp  Phe  Glu  His  Val  Lys  Asn  Ser  Thr  Tyr  Thr  Ala  Leu
 395                       400                 405                      410
 Ile  Ile  Ala  Thr  Asp  Asn  Gly  Ser  Pro  Val  Ala  Thr  Gly  Thr  Gly  Thr
                415                       420                      425
```

```
Leu Leu Leu Ile Leu Ser Asp Val Asn Asp Asn Ala Pro Ile Pro Glu
            430             435                     440

Pro Arg Thr Ile Phe Phe Cys Glu Arg Asn Pro Lys Pro Gln Val Ile
            445             450                 455

Asn Ile His Asp Ala Asp Leu Pro Pro Asn Thr Ser Pro Phe Thr Ala
    460                 465                 470

Glu Leu Thr His Gly Arg Val Pro Asn Trp Thr Ile Gln Tyr Asn Asp
475                     480             485                 490

Pro Thr Gln Glu Ser Ile Ile Leu Lys Pro Lys Met Ala Leu Glu Val
                495                 500                 505

Gly Asp Tyr Lys Ile Asn Leu Lys Leu Met Asp Asn Gln Asn Lys Asp
            510             515                 520

Gln Val Thr Thr Leu Glu Val Ser Val Cys Asp Cys Glu Gly Ala Ala
        525             530                 535

Gly Val Cys Arg Lys Ala Gln Pro Val Glu Ala Gly Leu Gln Ile Pro
    540             545             550

Ala Ile Leu Gly Ile Leu Gly Gly Ile Leu Ala Leu Leu Ile Leu Ile
555             560             565                     570

Leu Leu Leu Leu Leu Phe Leu Arg Arg Arg Ala Val Val Lys Glu Pro
            575             580                 585

Leu Leu Pro Pro Glu Asp Asp Thr Arg Asp Asn Val Tyr Tyr Tyr Asp
        590             595                 600

Glu Glu Gly Gly Gly Glu Glu Asp Gln Asp Phe Asp Leu Ser Gln Leu
        605             610                 615

His Arg Gly Leu Asp Ala Arg Pro Glu Val Thr Arg Asn Asp Val Ala
    620             625                 630

Pro Thr Leu Met Ser Val Pro Arg Tyr Leu Pro Arg Pro Ala Asn Pro
635             640             645                 650

Asp Glu Ile Gly Asn Phe Ile Asp Glu Asn Leu Lys Ala Ala Asp Thr
            655             660                 665

Asp Pro Thr Ala Pro Pro Tyr Asp Ser Leu Leu Val Phe Asp Tyr Glu
        670                 675                 680

Gly Ser Gly Ser Glu Ala Ala Ser Leu Ser Ser Leu Asn Ser Ser Glu
        685             690                 695

Ser Asp Lys Asp Gln Asp Tyr Asp Tyr Leu Asn Glu Trp Gly Asn Arg
    700             705                 710

Phe Lys Lys Leu Ala Asp Met Tyr Gly Gly Gly Glu Asp His
715             720             725
```